(12) United States Patent
Rastegar et al.

(10) Patent No.: US 9,970,844 B2
(45) Date of Patent: May 15, 2018

(54) MECHANICAL HIGH-G SHOCK TESTING MACHINES

(71) Applicants: Jahangir S Rastegar, Stony Brook, NY (US); Jacques Fischer, Sound Beach, NY (US)

(72) Inventors: Jahangir S Rastegar, Stony Brook, NY (US); Jacques Fischer, Sound Beach, NY (US)

(73) Assignee: OMNITEK PARTNERS LLC, Ronkonkoma, NY (US)

( * ) Notice: Subject to any disclaimer, the term of this patent is extended or adjusted under 35 U.S.C. 154(b) by 495 days.

(21) Appl. No.: 14/500,921

(22) Filed: Sep. 29, 2014

(65) Prior Publication Data

US 2016/0161362 A1   Jun. 9, 2016

Related U.S. Application Data

(60) Provisional application No. 61/884,915, filed on Sep. 30, 2013.

(51) Int. Cl.
*G01M 7/08* (2006.01)
*G01N 3/307* (2006.01)

(52) U.S. Cl.
CPC ............. *G01M 7/08* (2013.01); *G01N 3/307* (2013.01)

(58) Field of Classification Search
CPC .................................. G01M 7/08; G01N 3/307
USPC ....................... 73/12.01, 12.04, 12.06, 12.07
See application file for complete search history.

(56) References Cited

U.S. PATENT DOCUMENTS

| | | | | |
|---|---|---|---|---|
| 2,967,590 A * | 1/1961 | Ottestad | ............... | G01N 3/30 187/359 |
| 3,103,116 A * | 9/1963 | Kohli | ................. | G01N 3/303 188/67 |
| 3,226,974 A * | 1/1966 | Bresk | ................. | G01N 3/303 73/12.06 |
| 3,402,593 A * | 9/1968 | Bresk | ................. | G01N 3/303 188/316 |
| 3,421,361 A * | 1/1969 | Stowell | ................ | G01N 3/30 188/282.8 |
| 3,430,481 A * | 3/1969 | Shinbaum | ............ | G01M 7/08 73/12.04 |
| 3,485,083 A * | 12/1969 | Beal | ................... | G01N 3/303 267/139 |
| 3,577,763 A * | 5/1971 | Beal | ................... | G01N 3/303 73/12.06 |

* cited by examiner

*Primary Examiner* — Daniel S Larkin

(57) ABSTRACT

A shock testing machine including: a movable impact mass upon which one or more components to test are mounted; one or more rails upon which the impact mass is movable; and a brake operatively engageable with the movable impact mass after the movable impact mass has moved a predetermined distance to retard the movement of the movable impact mass such that the components to be tested experience a deceleration profile.

19 Claims, 29 Drawing Sheets

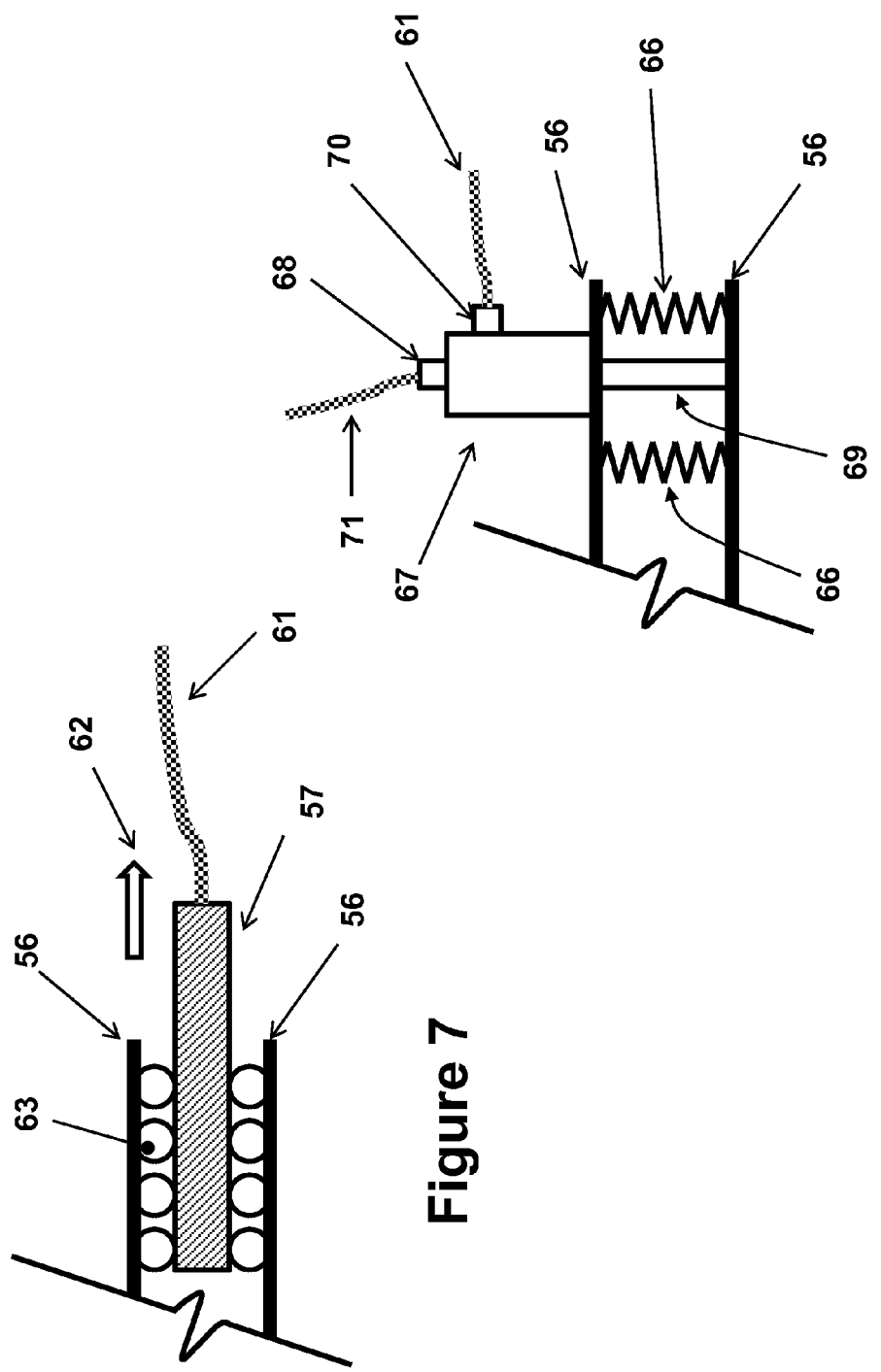

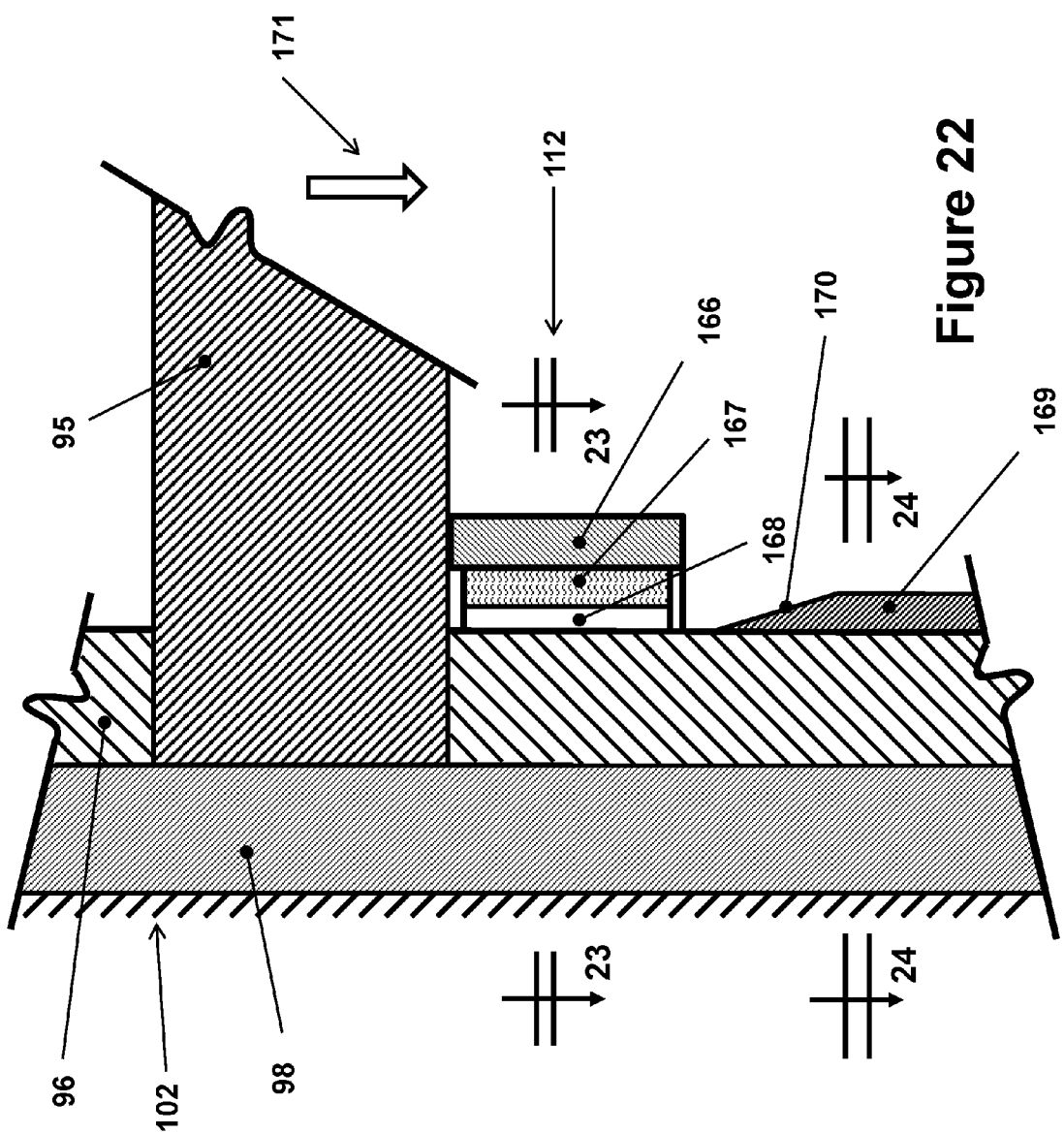

MECHANICAL HIGH-G SHOCK TESTING MACHINES

CROSS-REFERENCE TO RELATED APPLICATIONS

This application claims the benefit of priority to U.S. Provisional Application Ser. No. 61/884,915, filed on Sep. 30, 2013, the entire contents of which is incorporated herein by reference.

BACKGROUND OF THE INVENTION

1. Field of the Invention

The present invention relates generally to a shock and impact testing machine for subjecting the components to be tested to an acceleration pulse of a prescribed amplitude and duration, and more particularly for testing various devices and components of gun-fired or mortar or electrically powered rail gun or the like munitions as well said munitions by subjecting them to similar launch acceleration pulses.

2. Prior Art

Gun-fired munitions, mortars and rail-gun munitions are subjected to high-G (setback and set-forward) acceleration during the launch. Almost all munitions are also subjected to shock loading upon target impact. High-G shock loading is also experienced by rockets during launch and by spacecrafts during launch as well as pyrotechnic shock events during powered flight and deployment. As a result, all components of the system and the system itself must survive the shock loading events and be qualified to such severe environments.

Component qualification testing cannot obviously be done in an actual environment on complete assemblies. In addition to prohibitive cost involved, testing of components in actual environments would not provide the required information for determining the required component and system design margins. For these reasons, laboratory simulations of the shock loading environments are highly desirable for testing individual components, subassemblies and sometimes the complete system assembly.

In the current state of the art, shock loading environments are simulated in the industry by one of the following methods:

1. Electro-Dynamic Shaker.

This method can accurately produce a desired shock response spectrum (SRS) within closely specified tolerances, but amplitude and frequency limitations of the equipment greatly restrict its applicability.

2. Live Ordnance with System Structure.

Since the actual system structure and live ordnance are used, this method has the potential to produce a shock virtually identical to the expected field environment. The cost of the test structure, however, is usually prohibitive, unless large numbers of identical tests are to be conducted. The use of live ordnance may have a wide repeatability tolerance, and does not easily allow the test levels to be increased so that an adequate design margin can be assured. For the case of gun-fired munitions, mortars and the like, the added problem is the "soft" recovery of the launched round to examine the state of the components being tested. In certain case, telemetry of data may be used to transmit back data related to the operation of certain components. However, in most cases it is highly desirable to examine the state of the components post firing. In addition, in many cases it is extremely difficult if not impossible to measure/determine the effect of shock loading on many components for transmission to a ground station via telemetry.

3. Live Ordnance with Mock Structure.

This method has most of the same features as the method "2" above, except that some cost savings are attributed to the use of a mass mock-up structure. These savings may be negated by the need for some trial-and-error testing to attain the desired component input, where geometric similarity was used in method "2" above to attain the same result. This method also suffers from the same shortcomings for testing components of gun-fired munitions and mortars and the like as indicated for the above method "2".

4. Live Ordnance with Resonant Fixture.

This method further reduces test cost, and is a candidate for general purpose testing, due to the use of a generic resonant plate fixture. Since live ordnance is used, all the very high frequencies associated with near-field pyrotechnic shock events are produced with this method. However, a great amount of trial-and-error testing may be required to obtain the desired component input.

5. Mechanical Impact with Mock Structure.

Mechanical impacts do not produce the very high frequencies associated with the stress pulse in the immediate vicinity of a pyrotechnic device. However, most components in a typical system are isolated by enough intermediary structure such that the shock at the component location is not dominated by these very high frequencies. Instead, the shock at the component is dominated by the structural response to the pyrotechnic device, and has dominant frequencies which are typically less than 10 KHz. For these components, a mechanical impact (e.g. using a projectile or pendulum hammer) can produce a good simulation of the pyrotechnic shock environment. Test amplitudes can easily be increased or decreased by simply increasing or decreasing the impact speed. The shock level and duration can be controlled to some extent by the use of various pads affixed at the point of impact. According to this method, attempt is made to subject the structure containing the test components the impact induced acceleration (shock) profile, which close to that experienced when assembled in the actual system. The test conditions are experimentally adjusted to achieve an approximation of the actual acceleration (shock) profile. In general, a large amount of trial-and-error runs have to be made to achieve an acceptable acceleration (shock) profile. The characteristics and response of the various pads used at the impact point to increase the duration of the shock (acceleration) event is generally highly variable and dependent on temperature and moisture. In addition, due to inherent design of such mechanical impact machines and the limitations on the thickness of the pads that can be used at the impact point, high G acceleration peaks with long enough duration similar to those, e.g., experienced by munitions fired large caliber guns or mortars, cannot be achieved. For example, to achieve a peak shock acceleration level of 5000 G with a duration of 4 milliseconds, the pad deformation has to be well over 0.6 meters (considering a reasonable ramp-up and ramp-down of 0.1 meters each), which is highly impractical. It is also appreciated by those skilled in the art that for simulating firing (setback) acceleration for most gun-fired munitions and mortars, the peak acceleration levels can generally be well over the considered 5000 Gs with significantly longer durations. It can therefore be concluded that the described mechanical impact machines do not accurately duplicate the shock profile experienced by munitions during firing or target impact and are not suitable for accurate shock testing of components to be used in such munitions.

6. Mechanical Impact with Resonant Fixture.

In this method, a resonant fixture (typically a flat plate) is used instead of a mock structure. This significantly reduces cost, and allows for general purpose testing since the fixturing is not associated with a particular structural system. The mechanical impact excites the fixture into resonance which provides the desired input to a test component mounted on the fixture. Historically, test parameters such as plate geometry, component location, impact location and impact speed have been determined in a trial-and-error fashion. In general, this method produces a simulated environment which has its energy concentrated in a relatively narrow frequency bandwidth. It should be noted here that a suitable resonant fixture for use in this method may also be a bar impacted either at the end or at some point along the length of the bar. This method is suitable for many applications in which the components are subjected to relatively long term vibration such as those induced by the system structure. The method is, however, not suitable for testing components of gun-fired munitions and the like since in such cases the munitions is subjected primarily to a single very high G setback or impact shock with relatively long duration.

7. Air-Gun Testing Platforms.

In this method, the components to be tested are usually mounted in a "piston" like housing with appropriate geometry. In one method, the "piston" is then accelerated by the sudden release of pressurized air or accelerated by the rupture of a diaphragm behind which air pressure is continuously increased until the diaphragm is failed in sheared. In another type of air gun a similar air tight "piston" within which the components to be tested are securely mounted is accelerated over a certain length of a tube by pressurized gasses. The "piston" is thereby accelerated at relatively slower rates and once it has gained a prescribed velocity, the "piston" existing the tube and impacts decelerating pads of proper characteristics such as aluminum honeycomb structures to achieve the desired deceleration amplitude and duration. The components are assembled inside the "piston" such that the deceleration profile to correspond to the desired actual shock (acceleration) profile. In general, similar to the above method 5, air guns can be used to subject the test components to high G shock (acceleration) levels of over 30,000 Gs but for durations that are significantly lower than those experienced by gun-fired munitions, mortars and the like. It can therefore be concluded that the described mechanical impact machines do not accurately duplicate the shock profile experienced by munitions during firing or target impact and are not suitable for accurate shock testing of components to be used in such munitions.

8. Rocket Sleds.

Rocket sled is a test platform that slides along a set of rails, propelled by rockets. As its name implies, a rocket sled does not use wheels. Instead, it has sliding pads, called "slippers", which are curved around the head of the rails to prevent the sled from flying off the track. The rail cross-section profile is usually that of a Vignoles rail, commonly used for railroads. Rocket sleds are used extensively aerospace applications to accelerate equipment considered too experimental (hazardous) for testing directly in piloted aircraft. The equipment to be tested under high acceleration or high airspeed conditions are installed along with appropriate instrumentation, data recording and telemetry equipment on the sled. The sled is then accelerated according to the experiment's design requirements for data collection along a length of isolated, precisely level and straight test track. This system is not suitable for testing components for gun-fired munitions and mortars and the like since it can produce only around 100-200 Gs.

9. Soft Recovery System Facility (SCat Gun)

In this system, the components to be tested are packaged inside a round, which is fired by an actual gun (in the current system located at the U.S. Army Armament Research, Development and Engineering Center (ARDEC) in New Jersey, with a 155 mm round being fired by a 155 mm Howitzer weapon with a M199 gun tube and 540 feet of catch tubes). The projectile is then recovered using a "Soft Recovery" system. The soft catch component of the system uses both pressurized air and water to help slow down the projectile. The first part of the chain of catch tubes only contains atmospheric air. The next section, 320 feet of the tubes, contains pressurized air, followed by an 80 feet section that is filled with water. A small burst diaphragm seals one end of the pressurized air and a piston seals the other end. The piston also separates the water and pressurized air sections. The burst diaphragm and piston are replaced after each test fire. Once fired, the projectile achieves free flight for approximately 6 feet and travels down the catch tubes, generating shockwaves that interact with the atmospheric air section, the burst diaphragm, the pressurized air section, the piston and the water section. The air section is compressed and pushed forward and shock and pressure cause the piston move against the water, all while slowing the projectile to a stop. Then the piston is ejected out of the end of the system, followed by the air and water, and finally the projectile comes to rest in a mechanized brake system. On-board-recorders inside the projectile measure the accelerations of the projectile from the gun-launch and the catch events. This system is currently provides the means to subject the test components to as realistic firing shock loading conditions as possible and provide the means to retrieve the round to examine the tested components. The cost of each testing is, however, very high, thereby making it impractical for use for engineering development. The system is also impractical for use for most reliability testing in which hundreds and sometimes thousands of samples have to be tested and individually instrumented. It also takes hours to perform each test.

The methods 1-6 described above are more fully explained in the following references: Daniel R. Raichel, "Current Methods of Simulating Pyrotechnic Shock", Pasadena, Calif.: Jet Propulsion Laboratory, California Institute of Technology, Jul. 29, 1991; Monty Bai, and Wesley Thatcher, "High G Pyrotechnic Shock Simulation Using Metal-to-Metal Impact", The Shock and Vibration Bulletin, Bulletin 49, Part 1, Washington D.C.: The Shock and Vibration Information Center, September, 1979; Neil T. Davie, "The Controlled Response of Resonating Fixtures Used to Simulate Pyroshock Environments", The Shock and Vibration Bulletin, Bulletin 56, Part 3, Washington D.C.: The Shock and Vibration Information Center, Naval Research Laboratory, August 1986; Neil T. Davie, "Pyrotechnic Shock Simulation Using the Controlled Response of a Resonating Bar Fixture", Proceedings of the Institute of Environmental Sciences 31st Annual Technical Meeting, 1985; "The Shock and Vibration Handbook", Second Edition, page 1-14, Edited by C. M. Harris and C. E. Crede, New York: McGraw-Hill Book Co., 1976; Henry N. Luhrs, "Pyroshock Testing--Past and Future", Proceedings of the Institute of Environmental Sciences 27th Annual Technical Meeting, 1981.

The aforementioned currently available methods and systems for testing components to be used in systems that subject them to acceleration (shock) events have a number of shortcomings for use to simulate high G acceleration (shock) events with relatively long duration, such as those encountered in large caliber guns and mortars, for example, to simulate gun-firing events with setback accelerations of over 5,000 Gs and durations of around 5 milliseconds. Firstly, most of the available methods and devices, except those that are based on actual firing of the projectile from the actual gun or mortar or the like, cannot provide long enough acceleration pulse duration. Secondly, those methods that are based on actual firing of the projectile from the actual gun or mortar or the like have prohibitive cost, thereby making them impractical for engineering development tasks which requires countless iterations to achieve the desired results for individual components as well as for their assemblies. In addition, reliability tests for munitions components required testing of a very large number of components, which would make the total cost of munitions development prohibitive. Thirdly, in many component tests, it is highly desirable to instrument each component so that its behavior during the total shock environment can be monitored. Such instrumentation and monitoring is very difficult to achieve when the components to be tested have to be assembled in a rather small volume of fired projectiles.

A basic design of a mechanical shock testing machine 10 of the prior art that uses the aforementioned method "6" (Mechanical Impact with Resonant Fixture) is illustrated in the schematic of FIG. 1. The schematic of FIG. 1 is intended to show only the main components of such a mechanical shock testing machine. The mechanical shock machine 10 is constructed with some type of rails 12 along which the impact mass element 11 travels. The rails (one or more) may have any cross-sectional shape and the sliding surfaces between the mass element 11 and the rails 12 may be covered with low friction material or may utilize rolling elements to minimize sliding friction. The rails 12 are generally mounted on a relatively solid and massive base 13, which in turn rests on a firm foundation 14. Certain relatively stiff shock absorbing elements (not shown) may be provided between the base 13 and the ground 14 to prevent damage to the foundation structure. In heavier machinery, a relatively large (usually reinforced concrete) foundation block (not shown) is used with shock isolation elements having been positioned between the foundation block and the surrounding structure.

The components to be tested 15 are attached fixedly to the mass element 11, usually via a fixture 16. In the mechanical shock machine 10, the mass element 11 acts as a "hammer" that is designed to impact an anvil 17 to impart the desired shock loading (deceleration profile in the present mechanical shock testing machine) onto the components 15 that are to be tested. The anvil 17 is generally desired to be very rigid as well as massive and be securely attached to the base 13 of the mechanical shock testing machine. In many cases, the mass element 11 is provided with an impact element 18, which is designed to have a relatively sharp and hard tip 19.

To perform shock testing of the components 15, the mass element 11 ("hammer" element) is accelerated downwards in the direction of the arrow 20 towards the anvil 17. The shock testing machines are usually installed vertically. In which case and when relatively low impact shock (deceleration) levels or very short shock durations are desired, the mass element 11 is accelerated in the direction of the arrow 20 under the gravitational acceleration, with the height of travel determining the level of velocity attained by the mass element ("hammer") at the time of impacting the anvil 17. In other mechanical shock testing machines, particularly when higher mass element 11 velocity at impact velocity is desired, other means such as pre-tensioned bungee cords or pneumatic cylinders (not shown) are also used to significantly increase downward acceleration of the mass element 11 (in the direction of the arrow 20), thereby significantly increasing the impact speed between the mass element 11 (the "hammer" element) and the anvil 17. In those cases in which the mechanical shock testing machine 10 is installed horizontally (not shown), the mass element 11 is accelerated in the direction of the arrow 20 by the aforementioned pre-tensioned bungee cords, pneumatic cylinders or even linear motors.

The shock (deceleration) level experienced by the mass element 11 and thereby the test components 15 and its duration can be controlled to some extent by the use of various pads 21 affixed at the point of impact, i.e., between the anvil 17 surface and the impacting tip 19 of the impact element 18 of the mass element 11 ("hammer"). The shock (deceleration pulse) amplitude can also be increased or decreased by simply increasing or decreasing the impact speed. The test conditions are experimentally adjusted to achieve as close an approximation of the actual acceleration (shock) profile as possible.

SUMMARY OF THE INVENTION

A need therefore exists for the development of novel methods and resulting testing apparatus (shock testing machines) for testing components of gun-fired munitions, mortars and other devices and systems that are subjected high G acceleration (shock loading) with a relatively long duration such as projectiles fired by large caliber guns, mortars and the like. The developed methods should not be based on the use of the actual or similar platforms, for example, firing projectiles carrying the test components with similar guns such as the described in the method "9" above, due to the cost and difficulty in providing full instrumentation which would allow testing of a few components at a time, thereby making the cost of engineering development of such components and their reliability testing which requires testing of a large number of samples prohibitively high.

A need also exists for novel mechanical shock testing machines that can provide the means of testing a large number of fully instrumented components in a relatively short time. This requires that the mechanical shock testing machine allows rapid mounting of test components onto the test platform while allowing relatively free access to the components, unlike the "piston" platforms used in air guns (aforementioned method "7") or inside projectiles that are gun-launched (aforementioned method "9").

The novel mechanical sock testing must also provide highly predictable and repeatable shock loading (acceleration) provide for testing the intended components so that the results can be used for detailed analytical model validation and tuning; for predicting the performance of the components in actual applications; and for providing the required information for the design of the components and optimization of the developed designs.

Herein is described a novel method for the design of shock testing machines and the resulting shock testing machines that can subject test components and systems to high G acceleration pulse (shock) of relatively long duration. The resulting shock testing machines are shown to address the aforementioned needs and are particularly suitable for engineering development and testing of components to be used in gun-fired munitions, mortars and the like.

Accordingly, a shock testing machine is provided. The shock testing machine comprising: a movable impact mass upon which one or more components to test are mounted; one or more rails upon which the impact mass is movable; and a brake operatively engageable with the movable impact mass after the movable impact mass has moved a predetermined distance to retard the movement of the movable impact mass such that the components to be tested experience a deceleration profile.

The one or more rails can comprise two or more rails. The brake can comprises a brake element corresponding to each of the two or more rails.

The brake can be fixed to the movable impact mass. The brake can be movable on the one or more rails.

The one or more rails can comprise two or more rails and the brake can comprise a brake element corresponding to each of the two or more rails, in which case the shock testing machine can further comprise a rigid member connecting the brake elements such that the movable impact mass engages the brake elements at the same time after moving the predetermined distance.

The brake can be disposed on the one or more rails at the predetermined distance from the movable impact mass and the brake can be preset to be engaged with the one or more rails.

The brake can be mounted on the movable impact mass and the brake can be engaged with the one or more rails only after moving the predetermined distance.

The brake can at least partially surround an outer periphery of the one or more rails. The brake can include at least a circular portion for surrounding the outer periphery of the one or more rails.

The brake can include one or more first portions fixed to the movable impact mass that are engageable with one or more second portions fixed to a base structure.

The brake can include a cable having one end fixed to a base structure and another end removably connected to the brake, wherein the brake is engaged by movement of the movable impact mass through the predetermined distance tending to pull the another end from the brake.

The rails can be positioned vertically such that gravity assists the movement of the movable impact mass.

The rails can be positioned horizontally such that gravity does not assist the movement of the movable impact mass.

The movable impact mass can include a pocket for housing the one or more components to be tested.

The one or more rails can comprise two or more rails and the brake can comprise a brake element corresponding to each of the two or more rails, in which case the shock testing machine can further comprise a mechanism for applying equal pressure to each of the brake elements.

Also provided is a method for shock testing one or more components. The method comprising: mounting the one or more components to a movable impact mass; movably disposing the movable impact mass on one or more rails; moving the movable impact mass a predetermined distance; and engaging a brake after the movable impact mass has moved a predetermined distance to retard the movement of the movable impact mass such that the components to be tested experience a deceleration profile.

The brake can be disposed on the one or more rails at the predetermined distance from the movable impact mass and the brake can be preset to be engaged with the one or more rails.

The brake can be mounted on the movable impact mass and the brake can be engaged with the one or more rails only after moving the predetermined distance.

BRIEF DESCRIPTION OF THE DRAWINGS

These and other features, aspects, and advantages of the apparatus of the present invention will become better understood with regard to the following description, appended claims, and accompanying drawings where:

FIG. 7 illustrates the schematic of a brake engagement mechanism for the mechanical shock testing machine embodiment of FIG. 5.

FIG. 8 illustrates the schematic of another brake engagement mechanism for the mechanical shock testing machine embodiment of FIG. 5.

FIG. 22 illustrates another embodiment of the brake engagement mechanism of the mechanical shock testing machine of FIG. 12 with the braking elements attached to the mass element of the machine.

DETAILED DESCRIPTION

Figure 1:
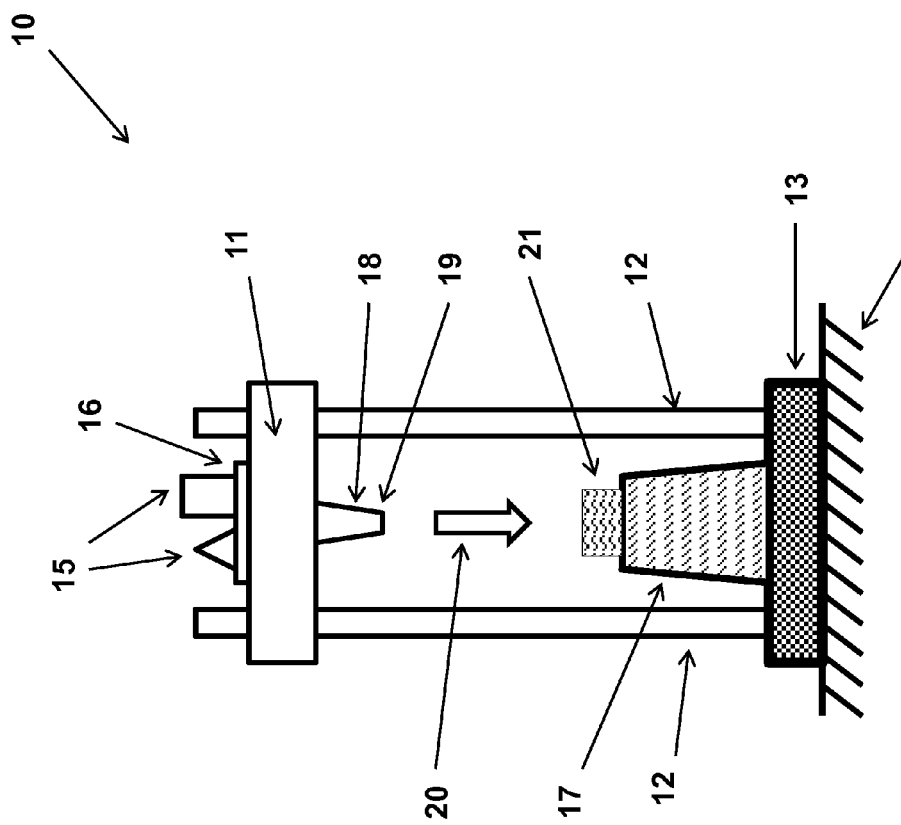
FIG. 1 illustrates the basic design of a mechanical shock testing machine of prior art.
Figure 2:
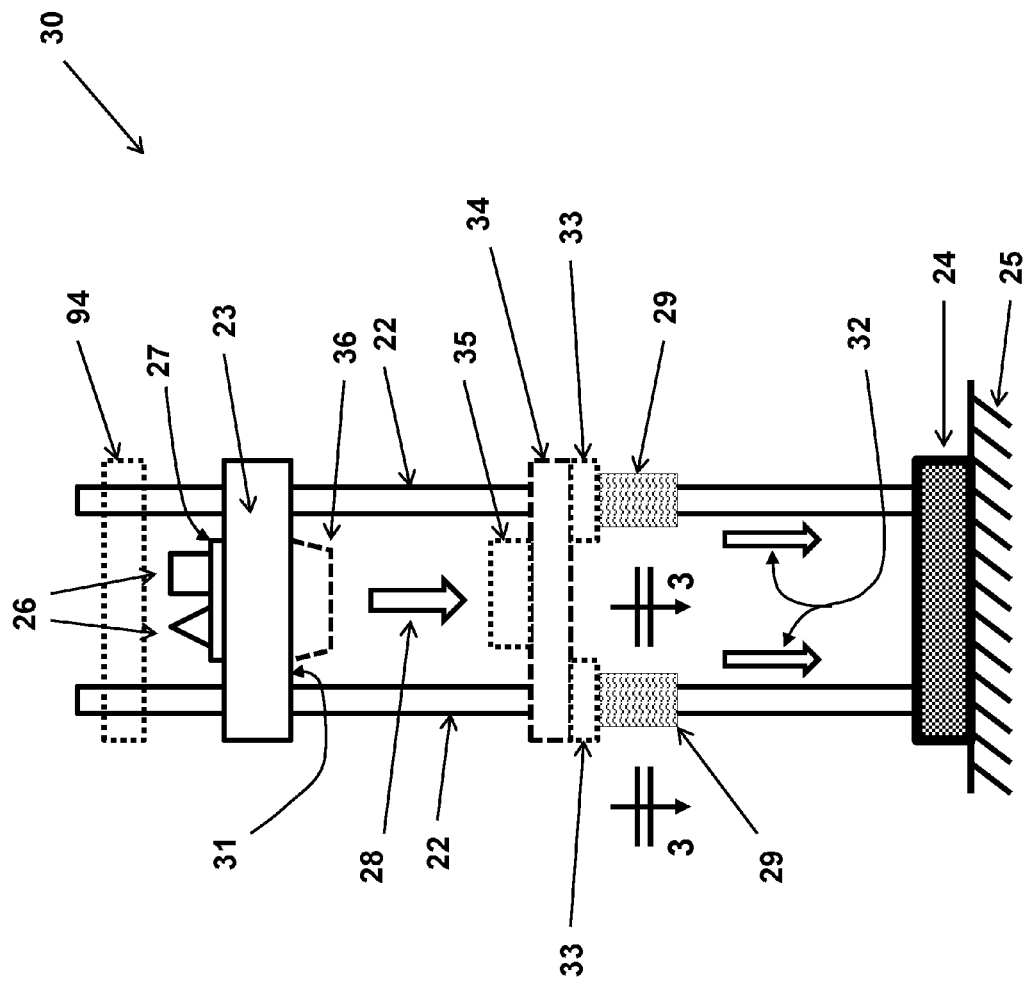
FIG. 2 illustrates the schematic of the first embodiment of the mechanical shock testing machine.

A schematic of a first mechanical shock testing machine embodiment 30 is shown in FIG. 2. The basic structure of the mechanical shock testing machine 30 is the same as the shock testing machine 10 of the prior art shown in the schematic of FIG. 1. The schematic of FIG. 2 is intended to show only the main components of the present mechanical shock testing machine 30. The mechanical shock machine 30 is similarly constructed with some type of rails 22 along which the impact mass element 23 travels. The rails (one or more) may have any cross-sectional shape and the sliding surfaces between the mass element 23 and the rails 22 may be covered with low friction material or may utilize rolling elements to minimize sliding friction. The rails 22 are generally mounted on a relatively solid and massive base 24, which in turns rests on a firm foundation 25. Certain relatively stiff shock absorbing elements (not shown) may be provided between the base 24 and the ground 25 to prevent damage to the foundation structure. In heavier machinery, a relatively large (usually reinforced concrete) foundation block (not shown) is used with shock isolation elements positioned between the foundation block and the surrounding structure.

The component(s) to be tested 26 is/are attached fixedly to the mass element 23, usually via a fixture 27. To perform shock testing of the components 26, the mass element 23 is similarly accelerated downwards in the direction of the arrow 28. The shock testing machines may be installed vertically, in which case and when relatively low impact shock (deceleration) levels are desired, the mass element 23 is accelerated in the direction of arrow 28 under gravitational acceleration. When using gravity to accelerate the mass element downwards, the height of vertical travel of the mass element 23 determines the level of velocity that is attained by the mass element 23. Alternatively, particularly when higher mass element 23 velocities are desired to be attained, other aforementioned means, such as pre-tensioned bungee cords or pneumatic cylinders (not shown), are also used to significantly increase downward acceleration of the mass element 23, thereby significantly increasing its attainable velocity for a length of travel. In the case of the present mechanical shock testing machine 30, for the reasons that are described later in this disclosure, the machine can be configured horizontally (i.e., the rails are horizontally installed so that the mass element 23 travels horizontally). In which case, the mass element 23 has to be accelerated by externally applied forces, such as by the aforementioned pre-tensioned bungee cords or pneumatic cylinders or even linear motors. In general, the means of accelerating the mass element 23 in the present mechanical shock testing machines can be the use of pre-tensioned bungee cords, which are simple to use, have a compact design, light weight, low cost, and ease of varying the force, among other reasons.

In the prior art mechanical shock machine 10, FIG. 1, the mass element 11 acts as a "hammer" that impact an anvil 17 at a certain appropriate velocity to impart the desired shock loading (deceleration profile) onto the components 15 that are being tested. The shock (deceleration) level experienced by the mass element 11 and thereby the test components 15 and its duration can be controlled to some extent by the use of various pads 21 affixed at the point of impact between the anvil 17 surface and the impacting tip 19 of the impact element 18 of the mass element 11. As was previously described, the use of such pads 21 between the impacting components can only provide very short duration shock loading (deceleration pulse) due to the limitations on the thickness of such pad 21 systems. In the embodiment 30, this shortcoming is eliminated.

In the embodiment 30 of the present mechanical shock testing machine, the shock testing machine is provided with brake elements 29, which are mounted on the rails 22 at a certain height as shown in the schematic of FIG. 2. The brakes elements 29 are positioned such that as the mass element 23 travels down, the bottom surface 31 of the mass element 23 engages the brake elements 29 essentially simultaneously. The brake elements 29 can be designed to have minimal mass, provide appropriate mechanisms to rapidly and accurately adjust the provided friction forces, and provide a relatively constant braking force with close static and dynamic coefficients of friction (examples of such braking elements and their various braking force adjustment mechanisms are provided below).

To perform shock testing of the components 26, the mass element 23 is accelerated downwards in the direction of the arrow 28 as was previously described. The mass element 23 while traveling at the predetermined velocity would engage the brake elements 29. If the mass of the brake elements 29 compared to the mass of the mass element 23 is negligible, then the braking force will begin to decelerate the mass element 23. If the braking force provided by the braking elements 29 and the mass of the mass element 23 are indicated as F and m, respectively, then the deceleration a of the mass element 23 and thereby the testing components is given as $$a = F/m$$

The mass element 23 together with the brake elements 29 will then travel down in the direction of the arrows 32 until they come to a stop. If the mass element 23 comes into contact with the brake elements 29 at the time t=0, and if the downward velocity of the mass element at this time is $V_1$, then the velocity $V_2$ of the mass element 23 until it comes to a stop is given by $$V_2 = V_1 - a\ t$$

It will be appreciated by those skilled in the art that the present method of decelerating the mass element 23 to which the components 26 that are being tested are attached and the fact that the brake elements 29 can freely travel the required length of the rails 22 while decelerating the mass element with a nearly constant acceleration level allows the present mechanical shock testing 30 to achieve relatively very long and nearly constant deceleration levels that would otherwise be impossible with any currently available impact based mechanical shock testing machines.

It will be appreciated by those skilled in the art that in the above formula, it is assumed that the mass of the braking elements is negligible as compared to the mass m of the mass element 23. However, if the mass of the brake elements relative to the mass of the mass element 23 is not negligible, as the mass element 23 comes into contact with the brake elements 29, the impact between the two elements will impart a shock (deceleration) pulse on the mass element 23. The amplitude and duration of the initial shock pulse is dependent on the mass of the brake elements 29 relative to the mass of the mass element 23. In cases where such initial shock loading is not desirable, its amplitude can be significantly reduced or if desired totally eliminated by providing resilient and high damping pads 33 (e.g., similar to the pads 21 described for the prior art mechanical shock testing machine of FIG. 1) above the brake elements 29. The pads 33 can be designed to smoothly increase their resistance to the downward travel of the mass element 23 until the resistance force equals to the braking force of the braking elements 29, at which time the braking elements 29 would begin to slide down the tracks 22, decelerating the mass element 23 (thereby the components 26 that are being tested) at an essentially constant rate.

Alternatively, a relatively rigid member 34 may be used to bridge over the brake elements 29. A resilient and high damping pad 35 or an appropriately pressurized air spring or the like can be provided on the surface of the rigid member 34 so that as the downward traveling mass element 23 engages the rigid member 34, its rate of increase in deceleration, i.e., jerk, is relatively small and smooth. The pad 35 will then smoothly increase its resistance to the downward travel of the mass element 23 until the resistance force equals to the braking force of the braking elements 29, at which time the braking elements 29 would begin to slide down the tracks 22, decelerating the mass element 23 (thereby the components 26 that are being tested) at an essentially constant rate. The pads 29 may also be used to assist the process. It will be appreciated by those skilled in the art that the total mass of the rigid member 34, braking elements 29 and the pad 35 is desired to be as small as possible relative to the mass of the mass element 23 to minimize the amount of kinetic energy of the mass element 29 that has to be absorbed by the resilient and high damping pad 35 (and pads 29, if present), thereby reducing the duration of the (nearly constant) deceleration that is applied to the mass element and thereby the test components 26 as the braking elements 29 are pushed downward along the rails 22. In addition, a relatively rigid protrusion 36 may be provided on the mass element 23 to concentrate pressure applied to the resilient and high damping pad 35 as it is engaged by the downward traveling mass element 23 during the above described shock testing of the components 26.

It will be appreciated by those skilled in the art that by providing the brake elements 29 for decelerating the mass element 23 as was described above, an essentially constant deceleration pulse (shock) can be achieved with the mechanical shock testing machine embodiment 30 shown schematically in FIG. 2. In addition, the duration of the deceleration pulse can be increased by simply increasing the initial velocity of the mass element 23 as it engages the braking elements 29. With the disclosed mechanical shock testing machine embodiment 30, relatively long deceleration pulse durations can be achieved since the length of the rails 22 under the braking elements 29 can be made arbitrarily long. This is in contrast with the amount of deformation that impact pads element 21 of the prior art mechanical testing machines shown in FIG. 1 can practically provide as was previously described, thereby significantly limiting the duration of deceleration pulses that the prior art mechanical shock testing machines can provide.

It will also be appreciated by those skilled in the art that since the braking force provided by the braking elements 29 is essentially constant as the braking elements are pushed down along the rails 22 by the mass element 23, therefore the deceleration of the mass element 23 stays essentially constant during this time (i.e., during the deceleration pulse duration). This is also in contrast with the prior art mechanical shock testing machines shown schematically in FIG. 1 in which it is almost impossible to design impact pads 21 such that their generated resisting force is constant at every speed of the impacting mass element 11 and at every depth of deformation of the impact pads.

In the embodiment 30 of FIG. 2, the braking elements 29 are desired to have minimal mass as was previously described to minimize the impact pulse generated as the mass element 23 comes into contact with the braking elements via the resilient and high damping pads 33 and until the braking elements begin to travel downward together with the mass element 23. The impact pulse becomes more severe when the resilient and high damping pads 33 are not provided.

Figure 3A:
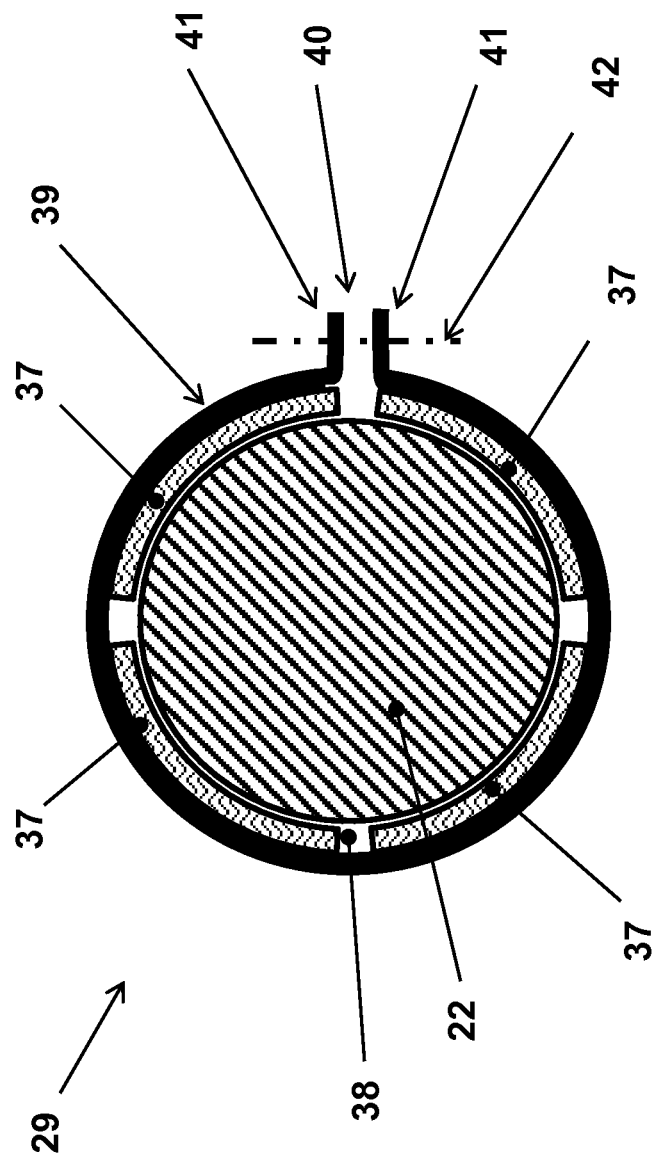
FIG. 3A illustrates cross-sectional view 3-3 of one possible design of the braking element of the mechanical shock testing machine of FIG. 2.

FIG. 3A illustrates the cross-sectional view 3-3 of an embodiment of the braking elements 29 designed for minimal mass and to provide a simple mechanism for adjusting the provided braking force. As can be seen in FIG. 3A, the braking element 29 consists of several braking pad segments 37 (in the schematic of FIG. 3A, four braking pad segments) that are in close contact with the surface of the rail 22. Gaps 38 can be provided between the braking pad segments 37 in the circumferential direction to minimize their interference during testing (as they slide down the rail 22) as well as while adjusting the braking pads 37 pressure on the surface of the rail 22 as described below.

It will be appreciated by those skilled in the art that numerous methods may be used to apply pressure to the braking pad segments 37 against the surface of the rail 22 to generate the desired braking forces. However, as previously discussed, it is highly desirable for the braking elements 29 to be as lightweight as possible to minimize the aforementioned impulsive impact forces generated as the mass element 23 comes into contact with the braking elements. A simple and lightweight and readily adjustable means of applying relatively uniform pressure to the braking pads 37 is a relatively thin (flexible) strap 39 of high strength material that is wrapped around the braking pads as shown in the schematic of FIG. 3A, leaving a small gap 40 open between extended ends 41 of the strap 39 to allow a bolt and nut fastener 42 (passing through holes provided in the extended ends 41—and collectively shown as the center line 42 for the sake of simplicity) to be tightened to generate the desired pressure on the braking pads 37. In general, since most braking pad materials are relatively soft and fragile, they are provided with relatively strong and stiff backing plates (collectively indicated as the braking pads 37) to ensure relatively uniform distribution of pressure generated by the straps 39. In addition, when the lengths of the braking pads 37 are relatively long, multiple and relatively narrow straps 39 can be used to ensure relatively uniform distribution of pressure between the pads 37 and surfaces of the rail 22.

It will be appreciated by those skilled in the art that the straps 39 and its bolt and nut fastener may be replaced by the commonly used and widely available "hose clamps". The use of such "hose clamps" can be generally designed to be lightweight, capable of generating relatively large forces, adjustable, have a relatively large range of diameter adjustment, low cost and readily available.

Figure 3B:
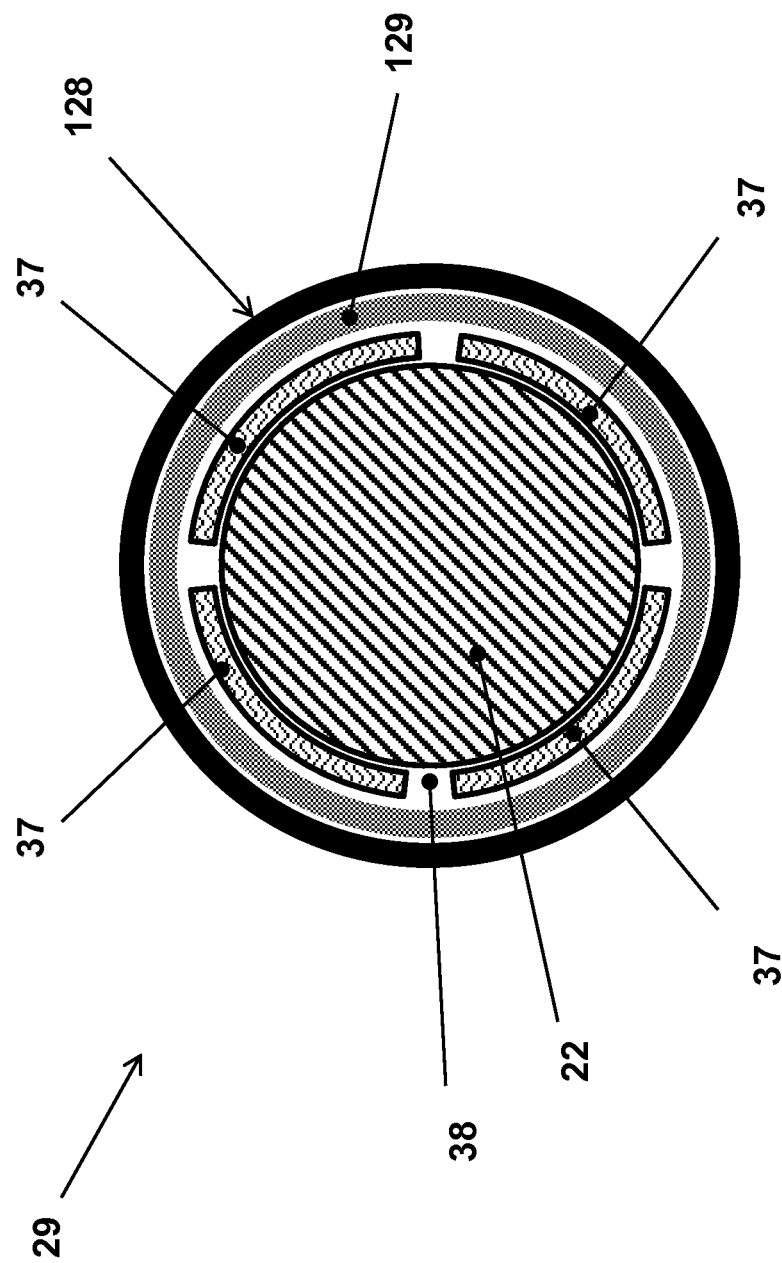
FIG. 3B illustrates cross-sectional view 3-3 of another possible design of the braking element of the mechanical shock testing machine of FIG. 2.

FIG. 3B illustrates the cross-sectional view 3-3 of another embodiment of the braking elements 29 designed for minimal mass and to provide a simple mechanism for adjusting the provided braking force. In the embodiment of FIG. 3B, similar to the embodiment of FIG. 3A, several braking pad segments 37 (in the schematic of FIG. 3B, four braking pad segments) that are in close contact with the surface of the rail 22 are used. Gaps 38 are similarly provided between the braking pad segments 37 to minimize their interference during testing (as they slide down the rail 22) as well as while adjusting the braking pads 37 pressure on the surface of the rail 22 as described below. To facilitate the braking element 29 assembly around the rails 22, a fabric or a thin elastomeric sheet (not shown), which may or may not be attached to the aforementioned relatively rigid backing supports of the braking elements 37, may be securely wrapped around the braking pad segments 37.

In this embodiment, a so-called pneumatic bag 129 (similar to pneumatic lifting bags or blood pressure measurement cuffs), commonly constructed with thin and flexible material with relatively inextensible layers is wrapped around the braking pad segments 37 (around the aforementioned holding fabric or a thin elastomeric sheet—if employed). A strong and relatively inextensible fabric or straps 128 are used to secure the pneumatic bag 129 as well as resist radial expansion of the pneumatic bag to allow it to be pressurized to the desired level. Then by pressurizing the pneumatic bags 129 through a one way valve similar to those for balls or those used for tires (not shown) to an appropriate level, the desired level of pressure is applied to the braking pad segments 37, thereby generating the desired level of braking forces between the braking elements 29 and the rails 22. The advantages of using such pneumatic bags 129 are their very lightweight; ease of pressure and thereby braking force adjustment; ease of assembly with the braking elements 37; and their availability and low cost. In addition, the use of the pneumatic bags 129 ensures highly uniform distribution of pressure between the pads 37 and surfaces of the rail 22.

In the mechanical shock testing machine embodiment 30 of FIG. 2, only one braking element 29 is shown to be used on each rail 22. To cover a large range of braking forces, particularly since the amount of pressure that can be applied to commonly used brake pad materials due to their relatively low maximum allowable contact pressure (usually around 300-500 psi), in one embodiment, the braking elements 29 can be fabricated with relatively short lengths (defined as the longitudinal length along the length of the rail 22). Then when larger braking forces are required, two or more such braking element assemblies are stacked along the longitudinal length of the rails and their pressures adjusted to provide the desired braking force. One advantage of using multiple such braking element assemblies is that their braking pad pressures over the rail surface can more readily be distributed uniformly; the individual brakes can be operated at lower contact pressure levels; thereby minimizing the rate of brake pad wears as well as local wear of the rail surfaces.

Figure 4:
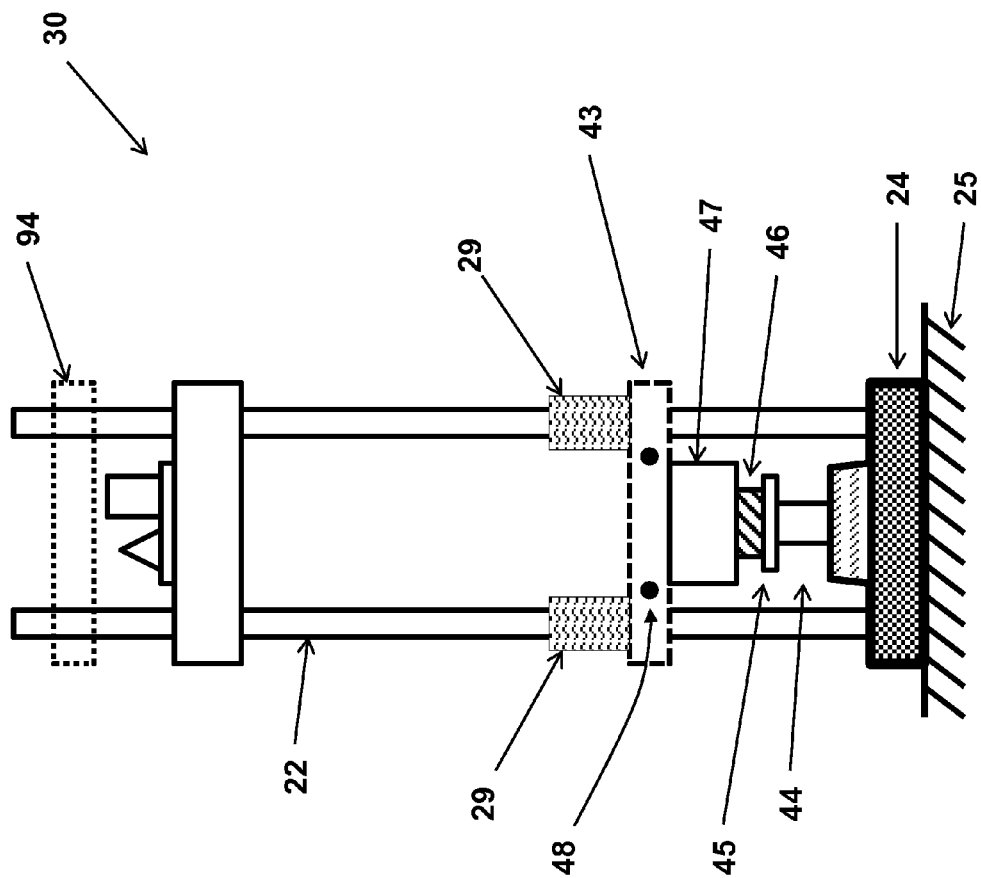
FIG. 4 illustrates the method and means of setting the braking force levels of the braking elements of the mechanical shock testing machine embodiment of FIG. 2.

The design of the mechanical shock testing machine embodiment 30 of FIG. 2 also allows for rapid and accurate setting of the braking force that is provided by the elements 29. A method and means of rapidly and accurately performing the brake force setting are described with reference to the schematic of FIG. 4. In FIG. 4, the mechanical shock testing machine embodiment 30 of FIG. 2 is shown together with a commonly used mechanical or hydraulic jack 44. The jack 44 is positioned over the base 24 and under the braking elements 29. A force gage 46 is positioned over a top platform 45 of the jack 44. A relatively rigid element 43 which is free to ride along the rails 22 is positioned under the braking elements 29. The element 43 can be fabricated in two halves (not shown) that are assembled by attaching them together by the bolts 48 to accommodate the rails 22 and to remove after brake force setting. A relatively stiff spring element 47 is provided between the relatively rigid element 43 bridging the braking elements 29 and the force gage 46. The spring element 47 can be fabricated using several helical compressive elements that are assembled between top and bottom plates (not shown). The entire jack 44, force gage 46 and spring element 47 assembly is centered between the rails 22. Then by raising the jack 44 (i.e., its top platform 45), the spring element 47 is compressed, thereby causing the relatively rigid element 43 to apply an essentially equal force to each of the braking elements 29, while the applied force is being measured by the force gage 46. As the force being transmitted to the braking elements 29 is increased by raising the jack 44, at a certain point the braking elements will begin to slide over the rails 22. The force reading of the force gage 46 at this point indicates the braking force that is provided by the braking elements 29. Further raisings of the jack 44 should indicate the same braking force reading. The braking force that is provided by the braking elements may now be adjusted by tightening or loosening the bolt and nut 42 for the embodiment of FIG. 3A and by adjusting the air (gas) pressure in the pneumatic bags 129 for the embodiment of FIG. 3B.

Figure 5:
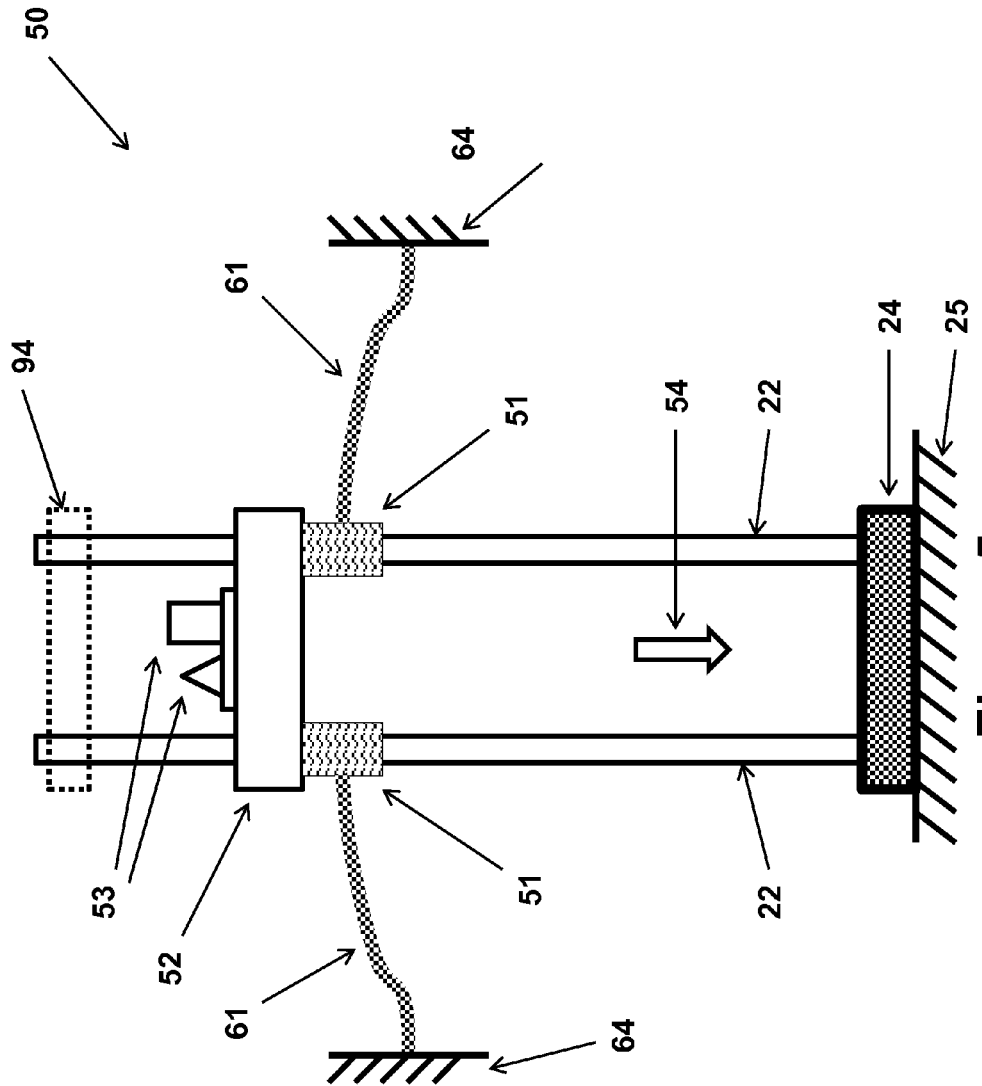
FIG. 5 illustrates the schematic of the second embodiment of the mechanical shock testing machine.

A second embodiment 50 of the mechanical shock testing machine is shown schematically in FIG. 5. All components of the mechanical shock testing machine 50 are the same as those of the embodiment 30 of FIG. 2, except for the braking elements 51 (29 in the embodiment of FIG. 2) which are different in design and are fixedly attached to the mass element 52 (23 in the embodiment of FIG. 2).

In the mechanical shock testing embodiment 50, the braking elements 51 are initially applying no braking force to the rails 22, i.e., the brake pads (similar to the pads 37 shown in FIG. 3A) are not pressed against the surface of the rails 22. This would therefore allow the assembly of the mass element 52 and braking elements 51 to be accelerated downwards (under gravity for vertically installed shock testing machines and/or pre-tensioned bungee cords or pneumatic cylinders or other similar means as was previously described) to gain a predetermined velocity. Then once the mass element and braking element assembly has gained the predetermined velocity, the braking elements 51 are engaged and begin to apply a prescribed level of braking force to the rails 22, thereby causing the mass element 52 to be decelerated at the desired rate, thereby subjecting the testing components 53 to a predetermined and essentially constant deceleration (shock) pulse that lasts until the assembly of the mass element 52 and braking elements 51 come to rest as was previously described for the embodiment of FIG. 2. The methods of designing and constructing the braking elements 51 and mechanisms for their activation once the mass element 52 has gained the prescribed velocity is described below.

An advantage of attaching the braking elements 51 to the mass element 52 is the elimination of the aforementioned impact shock (deceleration) pulse on the mass element 52 when it would have otherwise come into contact with stationary braking elements (as was previously described for the mass element 23 of the embodiment of FIG. 2 as it engages the stationary braking elements 29). In addition, it is generally difficult to totally eliminate the impact shock pulses and the generated ringing noise that it would generate. In addition, the use of resilient and high damping pads 33 in the embodiment of FIG. 2 between the mass element 23 and the braking elements 29 results in a significant dissipation of the kinetic energy of the mass element 23, thereby significantly reducing the level of shock (deceleration) and duration that can be achieved, and thereby requiring a higher initial velocity for the same shock loading level and duration.

As it was indicated above, in the mechanical shock testing embodiment 50, the braking elements 51 are initially applying no braking force to the rails 22. This would allow the assembly of mass element 52 and braking elements 51 to be freely accelerated downward in the direction of the arrow 54 using one of the aforementioned methods and means. It will be appreciated by those skilled in the art that numerous methods and means are known in the art that can be used to provide the braking elements 51 with the capability of being engaged while the mass element and braking elements assembly is traveling down in the direction of the arrow 54.

It will appreciated by those skilled in the art that since the mass element 52 would be traveling down at high velocities while the braking elements 51 are engaged (i.e., to begin to apply braking force by pressing the braking pads 37 against the surface of the rails 22), therefore the engagement mechanisms of the braking elements must be capable of engaging the braking elements 51 very rapidly to firstly minimize the downward travel distance of the mass element 52 before the brakes are fully engaged, i.e., until the desired mass element 52 deceleration level has been reached. The travel distance during braking engagement must be minimized to minimize the required total length of the rails 22. Secondly, while the braking forces applied by the braking elements 51 are building up as the braking elements 51 are being engaged, the assembly of mass element 52 and braking elements 51 is being decelerated, even though at slower rates than the prescribed shock testing (deceleration pulse) levels, thereby reducing (wasting) the kinetic energy of the mass element and braking elements assembly and thereby reducing the duration of the testing deceleration pulse.

Figure 6:
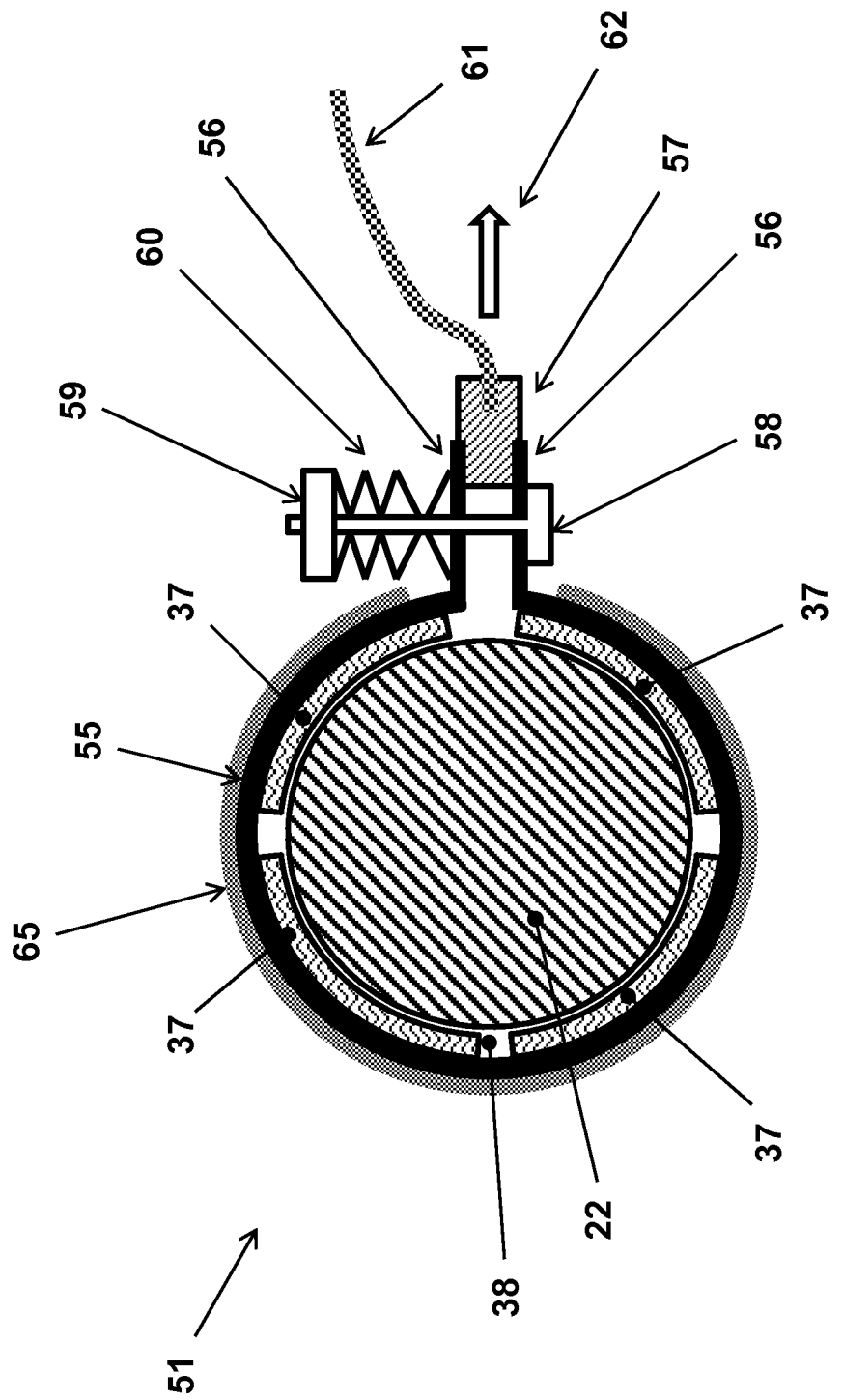
FIG. 6 illustrates the schematic of the basic design and operation of the braking elements for the mechanical shock testing machine embodiment of FIG. 5.

One mechanism for engaging the braking elements 51 once the mass element 52 and braking element 51 assembly has gained a predetermined velocity is shown schematically in FIG. 6. All components of the braking element assembly 51 is identical to that of the braking element 29 of FIG. 2, except that the bolt and nut fastener 42 used to generate the desired pressure on the braking pads 37 are replaced as described below.

As can be seen in the schematic of FIG. 6, the relatively thin (flexible) strap 55 (element 39 in the embodiment 29 of FIG. 4) which is made out of high strength material (such as spring steel) is provided with extended ends 56. A spacing element 57 is positioned between the extended ends 56. A pair of bolt 58 and nut 59 is passed through provided holes (not shown) in the extended ends 56, and is used to preload a compressive spring 60. The spacing element 57 can be provided with a slight wedging angle to make it easier to be pulled out from between the extended ends 56 in the direction of an arrow 62 by a cable 61. Once the spacing element 57 has been pulled out, the preloaded compressive spring 60 would apply a force to the extended ends 56 that tends to bring them together, thereby applying a compressive force to the brake pads 37, thereby generating the desired braking force between the braking elements 51 and the rails 22 to begin to decelerate the mass element 52 and braking element 51 assembly, thereby decelerating the testing components 53 at the prescribed rate.

It will be appreciated by those skilled in the art that the compressive spring 60 used in the braking element 51 is desired to be small and lightweight, and also capable of applying relatively large compressive forces to the extended ends 56 of the strap 55 of the braking element 51. In addition, by minimizing the mass of the compressive spring 60 and its required deflection once the spacing element 57 is pulled out, the total time for the braking element engagement is also minimized.

In addition, the force in the direction of the arrow 62 with which the cable 61 would need to pull the spacing element 57 out from between the extended ends 56 of the strap 55 to engage the braking element 51 is desired to be low to simplify the pulling mechanism for the cable 61 and minimize the total time for the braking element engagement. For these reasons, one may also provide sliding balls or rollers 63 between the surfaces of the extended ends 56 and the spacing element 57 as shown in the schematic of FIG. 7. As a result, the pulling cable 61 requires exerting minimal pulling force in the direction of the arrow 62 to release the spacing element 57.

In the mechanical shock testing machine embodiment 50, the free ends of the cables 61 of the braking element assembly (FIGS. 6 and 7) are attached to the machine structure (indicated with numeral 64 in FIG. 5). Then as the assembly of the mass element 52 and braking elements 51 is accelerated downwards in the direction of the arrow 54 as was previously described, when the assembly has gained a predetermined velocity, the free length of the cables 61 is adjusted to almost simultaneously engage the braking elements 51 by pulling the spacing elements 57 from between the extended ends 56 of the straps 55 of the braking elements 51, FIGS. 6-7.

In the schematics of FIGS. 6 and 7, a spacing element 57 is shown to be positioned between the extended ends 56 of the strap 55 of each braking element 51, that once removed, would allow the compressively preloaded spring 60 to apply pressure to the brake pads 37 via the strap 55 as was previously described.

In an alternative embodiment, the braking element is provided with at least one "C" shaped spring element 65, FIG. 6, which is preloaded to provide the desired level of compressive pressure on the braking pads 37 over the surface of the rails 22 once the spacing element 57 is pulled out from between the extended ends 56 of the strap 55 of each braking element 51. The advantages of using the aforementioned at least one "C" shaped spring element 65 include the design simplicity and the elimination of the bolt 58, nut 59 and the compressive spring 60. The shortcoming of the use of the at least one "C" shaped spring element 65 is the lack of means to readily adjust the spring preloading levels. One method of addressing this shortcoming is the use of several such "C" shaped spring elements 65, with different preloading levels to achieve the desired total preloading forces.

In another alternative embodiment, the extended ends 56 of the strap 55 of the braking elements 51 are provided with a linear actuation device 67 as shown in FIG. 8. The linear actuation device 67 may be of any type known in the art, for example, it may be a pneumatic piston (such as a diaphragm type to generate large levels of force with small stroke); or may be a hydraulic cylinder type; a piezoelectric (electrostrictive) or magnetostrictive type linear actuator; solenoid or any other type of similar linear or rotary electrical motor based type; or the like. The main desired characteristics of the linear actuation devices to be used are being lightweight; very fast acting; easy to adjust the force; and ease of activation or deactivation depending how it is used in the present brake element engagement mechanisms. In the present description, the linear actuator 67 is considered to be of a pneumatic type, however, the linear actuator may be of any other of the aforementioned types.

In the embodiment shown in FIG. 8, at least one pre-tensioned tension spring 66 is used to provide the desired brake pad 37 pressure over the surfaces of the rails 22 to generate the required braking forces for the desired mass element 52 deceleration levels. In this arrangement, the linear actuator 67 is used to counter the tension force of the springs 66 and eliminate the braking force of each braking element 51. This is accomplished by pressurizing the pneumatic cylinder 67 via its inlet port 68, which is considered to be equipped with a one-way valve that only allows air flow into the cylinder (piston). The piston rod 69 of the pressurized pneumatic actuator will then tend to force the extended ends 56 of the strap 55 of each braking element 51 apart, thereby overcoming the tension force of the springs 66. The assembly of the mass element 52 and braking elements 51 can then be accelerated downwards using one of the aforementioned methods with the disengaged braking elements 51. Then once the mass element 52 has gained its desired downward velocity in the direction of the arrow 54, the cable 61 is pulled as was described previously for the embodiments of FIGS. 6 and 7, thereby opening the relieve valve 70, depressurizing the pneumatic cylinder 67, thereby allowing the springs 66 to engage each braking element 51 and the resulting braking forces to begin to decelerate the assembly of the mass element 52 and braking elements 51 and thereby the components 53 that are to be tested.

It will be appreciated by those skilled in the art that at least one "C" shaped spring element 65 shown in the schematic of FIG. 5 may be used instead or in addition to the pre-tensioned tension spring 66 in the above embodiment shown in FIG. 8.

Alternatively, the pneumatic cylinder 67 may be used without the aforementioned pre-tensioned tension spring 66. In this configuration, the extended ends 56 of the strap 55 of each braking element 51 are normally positioned such that the braking pads 37 are not pressing against the surfaces of the rails 22, i.e., the braking elements 51 are disengaged. The mass element 52 is thereby free to be accelerated downwards as previously described. Then once the mass element 52 has gained its desired downward velocity in the direction of the arrow 54, the cable 61 is pulled as was described previously for the embodiments of FIGS. 6 and 7. In this configuration, each cable 61 is connected to a pneumatic valve (not shown) that is opened by the pulling of each cable 61, thereby allowing pressurized air (gas) to enter the pneumatic cylinder 67 through the line 71 and inlet 68. In this case, each pneumatic cylinder 67 is pressurized to retract the piston rod, thereby tending to close the gap between the extended ends 56 of each strap 55 of the braking elements 51, thereby engaging the braking elements 51. The applied braking forces will then begin to decelerate the assembly of the mass element 52 and braking elements 51 and thereby the components 53 that are to be tested.

It will be appreciated by those skilled in the art that among the above two configurations described for the braking element engagement mechanism of FIG. 8, the former option which uses the pre-tensioned tension spring elements 66 for generating the required braking pressure on the braking pads 37 can be superior in terms of speed of brake engagement and since it does not require a traveling pressurized hose 71. An advantage of the latter configuration is the ease with which the braking pressure can be adjusted by properly setting the inlet air pressure into the pneumatic cylinder 67.

It will also be appreciated by those skilled in the art that as was previously indicated, almost any other type of linear actuator may also be used in any one of the above configurations described in the braking element 51 engagement mechanism of FIG. 8. Of the previously indicated linear actuator types, the piezoelectric (electrostrictive) based linear actuation devices are of particular interest due to their very fast response time, for example a fraction of a millisecond for travel distances of a few millimeters. The main disadvantage of using such linear actuation devices directly in the braking element engagement mechanism of FIG. 8 is the limited displacement of such actuators and therefore the need to mechanically amplify their displacement.

Figure 9:
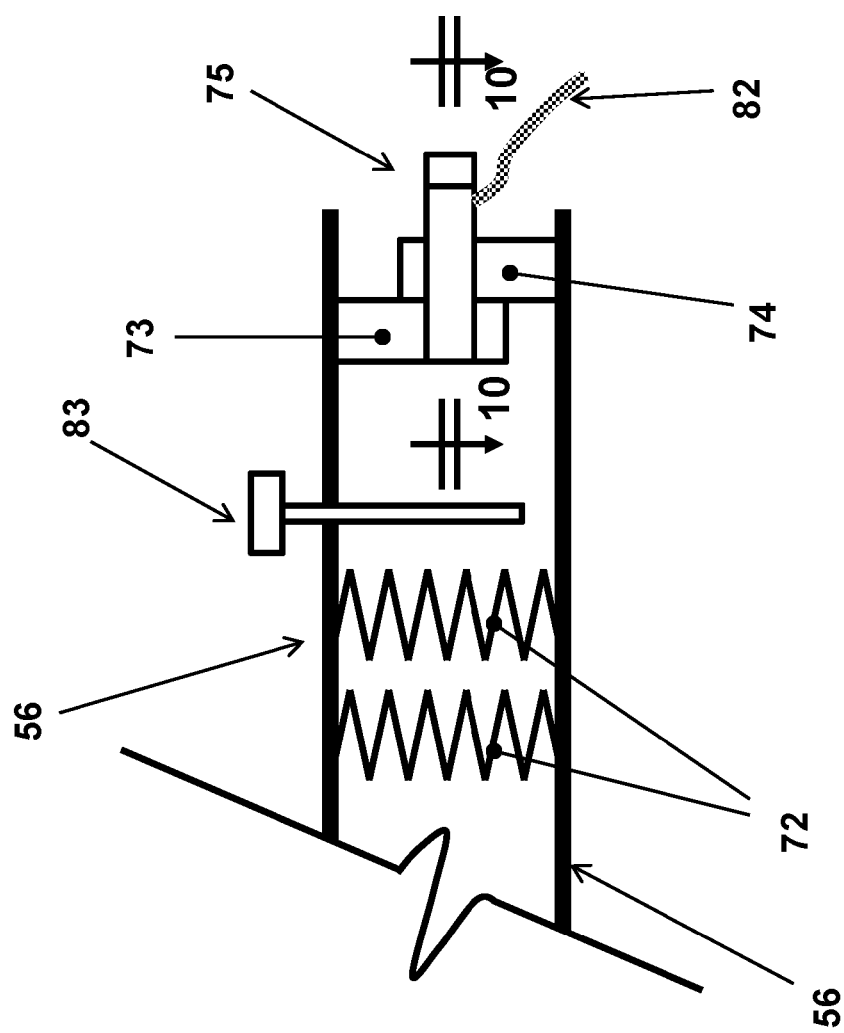
FIG. 9 illustrates the schematic of another brake engagement mechanism with piezoelectric actuation device for the mechanical shock testing machine embodiment of FIG. 5.
Figure 10:
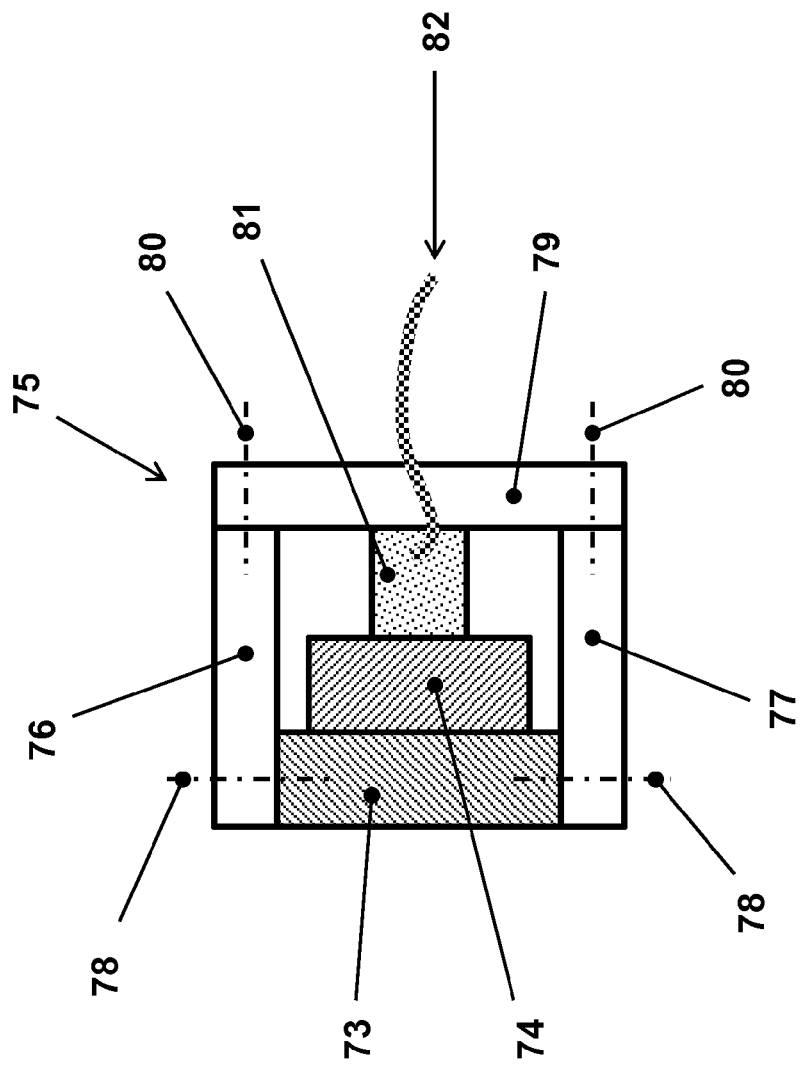
FIG. 10 illustrates the schematic of cross-sectional view 10-10 of the piezoelectric actuated clamping device of the brake engagement mechanism of FIG. 9.

Piezoelectric type actuation devices can, however, provide very large forces. This characteristic of piezoelectric actuation devices can be used in the braking element engagement mechanism that is shown in the schematic of FIG. 9. In this embodiment, the braking engagement mechanism of the braking elements 51 uses piezoelectric elements to actuate as shown in FIG. 9 and its cross-sectional view 10-10, as shown in FIG. 10. As can be seen in FIG. 9, at least one pre-tensioned tension spring 72 is between the extended ends 56 of the strap 55 of the braking elements 51 to provide the desired brake pad 37 pressure over the surfaces of the rails 22 to generate the required braking forces for the desired mass element 52 deceleration levels. Relatively rigid block elements 73 and 74 are attached to each of the extended ends 56 of the strap 55 of the braking elements 51 as shown in FIG. 9. A locking clamp 75 is also provided that can be used to firmly clamp the block elements 73 and 74 together to prevent their relative motion as will be described below. Then to keep the braking element 51 disengaged and allow for free downward movement of the mass element 52, the extended ends 56 are separated, subjecting the tensile springs 72 to further tension, and when the brake pads 37 no longer are pressing on the surfaces of the rail 22, the two block elements 73 and 74 are clamped together firmly to keep the braking element 51 in the disengaged state.

The design of the aforementioned piezoelectric actuated locking clamp 75 can be seen in the cross-sectional view 10-10 of FIG. 9 that is shown in FIG. 10. As can be seen in FIG. 10, the clamp 75 consists of two relatively rigid side elements 76 and 77, which are rigidly attached to the block 73, such as by welds, to prevent any relative motion and to minimize the total size, or by fasteners 78 and pins (not shown) to minimize relative motion. The relatively rigid plate 79 is then attached to the ends of the side elements 76 and 77 as shown in FIG. 10, such as by welds to prevent any relative motion and to minimize the total size, or by fasteners 80 and pins (not shown) to minimize relative motion. In practice, the sides 76 and 77 and the plate 79 and even the block 73 can be integrated as one piece to minimize the total size and mass of the braking elements 51. A piezoelectric actuator element 81 is then positioned between the plate 79 and the block 74 such that when the piezoelectric actuator 81 is energized by an appropriate voltage signal and increases its length axially, it would press the blocks 73 and 74 together firmly to prevent them from undergoing relative motion by the forces applied by the pre-tensioned tensile springs 72 (FIG. 9). In FIGS. 9 and 10, the wire 82 indicates the electrical wires through which voltage is applied to the piezoelectric actuator 81 to apply the force to "lock" the blocks 73 and 74 together. In this embodiment of the braking elements 51, the cable 61 (FIG. 5) is considered to be attached to the wire 82) and when pulled can disconnect power to the piezoelectric actuator 81 by, for example by actuating an electric switch or by disengaging a connector or the like well known in the art (not shown). In an embodiment, a friction increasing coating such as those made out of hard rubber or the like is used on the contacting surfaces of the blocks 73 and 74 to increase the level of friction between the surfaces.

The piezoelectric actuator based brake engagement mechanism shown in FIGS. 9 and 10 for the braking elements 51 of the mechanical shock testing machine of FIG. 5 will perform shock testing of the intended components as follows. The at least one pre-tensioned tension springs 72 are adjusted to proper tension levels to provide the desired braking forces once engaged as previously described. The extended ends 56 of the strap 55 of the braking elements 51, FIG. 9, are forced to separate until the braking pads 37 no longer apply any pressure to the surfaces of the rails 22. The piezoelectric actuator 81 is then energized, locking the blocks 73 and 74, thereby allowing the assembly of the mass element 52 and braking elements 51 to be free to travel over the rails 22, FIG. 5. The mass element 52 is then accelerated downwards as was previously described. Then once the mass element 52 has gained its desired downward velocity in the direction of the arrow 54, FIG. 5, the cable 61 is pulled as was described previously for the embodiments of FIGS. 6 and 7, thereby de-energizing the piezoelectric actuator 81 and allowing free displacement between the blocks 73 and 74. The at least one pre-tensioned tension springs 72 are then free to apply their pre-calibrated force to the extended ends 56 of the strap 55 of the braking elements 51, thereby engaging the braking elements 51. The applied braking forces will then begin to decelerate the assembly of the mass element 52 and braking elements 51 and thereby the components 53 that are to be tested as was described for the previous embodiments.

To disengage the braking elements 51 following pre-tensioning the at least one tension spring 72, FIG. 9, the extended ends 56 of the strap 55 of the braking elements 51 are forced to separate until the braking pads 37 no longer apply any pressure to the surfaces of the rails 22 as was indicated above. When the level of the force that has to be overcome is relatively high, the task is performed with the aid of assisting devices. Using such assistive devices would also help keep the extended ends 56 in position while the piezoelectric actuator based clamping mechanism is activated. It will be appreciated by those skilled in the art that numerous pneumatic, hydraulic, electrical and pure mechanical mechanisms that are well known in the art are available for this purpose. For example, a pneumatic or mechanical jack type or extractor type mechanism may be used for this purpose. Alternatively, a simple bolt 83 that is threaded on one of the extended ends 56 may be used to provide the above separation force.

It will be appreciated by those skilled in the art that the piezoelectric actuator based brake engagement mechanism of FIGS. 9 and 10 has the advantage of being lightweight and very fast acting for very high shock level and/or very long duration deceleration pulse testing.

In the embodiment of FIGS. 9 and 10, the piezoelectric actuator 81 is shown to be used to provide the described "locking" force to prevent relative motion between the blocks 73 and 74 to prevent the at least one pre-tensioned tension spring 72 to apply braking force via the brake pads 37, i.e., to keep the braking elements 51 disengaged. It will be, however, appreciated by those skilled in the art that other types of actuation mechanisms such as those based on magnetostrictive materials, pneumatic or hydraulic pistons, or the like may also be used for the same purposes.

Figure 11:
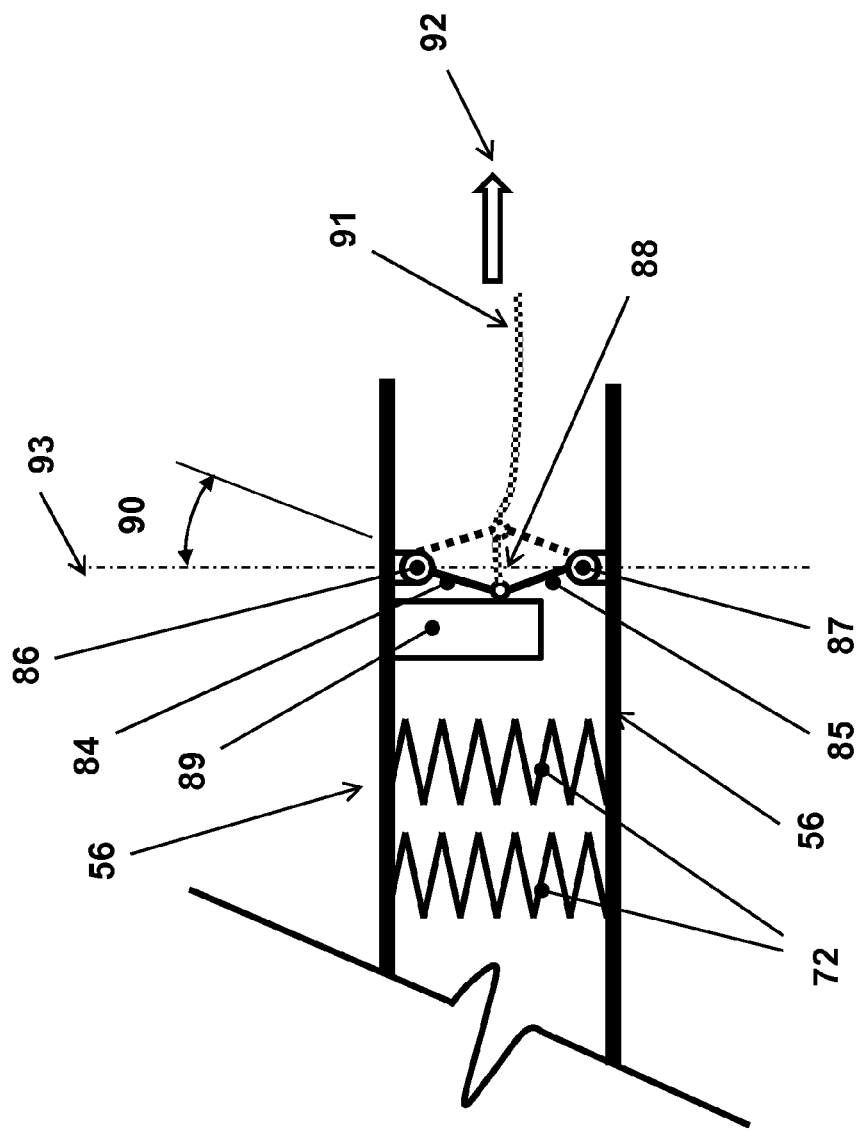
FIG. 11 illustrates the schematic of another brake linkage type engagement mechanism for the mechanical shock testing machine embodiment of FIG. 5.

In another embodiment of the brake engagement mechanism shown in the schematic of FIG. 11, the piezoelectric actuator based mechanism of FIGS. 9 and 10 is replaced with the linkage mechanism. The at least one pre-tensioned tension spring 72 is still mounted between the extended ends 56 of the strap 55 of the braking elements 51 to provide the desired brake pad 37 pressure over the surfaces of the rails 22 to generate the required braking forces for the desired mass element 52 deceleration levels. The linkage mechanism of this brake engagement mechanism consists of two links 84 and 85, which can be of equal lengths, and which are attached to each of the extended ends 56 of the strap 55 of the braking elements 51 by pin joints 86 and 87, respectively, as shown in the schematic of FIG. 11. The two links 84 and 85 are in turn attached together by the pin joint 88.

Then to keep the braking element 51 disengaged and allow for free downward movement of the mass element 52, the extended ends 56 are separated, subjecting the tensile springs 72 to further tension, until the brake pads 37 no longer apply pressure to the surfaces of the rail 22. The stiffness of the at least one tensile spring 72 and the lengths of the two links 84 and 85 are selected such that at this state of the extended ends 56, the links 84 and 85 can be positioned in the configuration shown in FIG. 11 with the one or both links or their connecting joint 88 resting against a relatively rigid block 89 as can be seen in FIG. 11. It will be appreciated by those skilled in the art that in the configuration shown in FIG. 11, the forces exerted by the tensile springs 72 is supported by the links 84 and 85 since the forces would tend to press the connecting joint 88 (or one or both links 84 and 85) against the stop block 89. It will also be appreciated by those skilled in the art that by ensuring that in the configuration of the links 84 and 85 the angle 90 that the links make with the line 93 passing through their joints 86 and 87 is relatively small, such as around 5-10 degrees, therefore the lateral force required to be applied to the joint 88 (in this case by the cable 91) in the direction of the arrow 92 in order to displace the joint 88 from its indicated position in FIG. 11 (to the left of the line 93) passed through the singular position (i.e., lined up with the line 93) of the links 84 and 85 and moved towards the right side of the line 93 as shown by the dotted line. Once the links 84 and 85 are brought past their singular position, they can no longer oppose the forces applied by the at least one tensile springs 72, and braking elements 52 are rapidly engaged.

To perform shock testing, the braking elements 51 are placed in their disengaged state as was described above, i.e., with the links 84 and 85 in their configuration shown with solid lines in FIG. 11. The assembly of the mass element 52 and braking elements 51 can then be accelerated downwards using one of the aforementioned methods with the disengaged braking elements 51. Then once the mass element 52 has gained its desired downward velocity in the direction of the arrow 54 (see FIG. 5), the cable 91 is pulled in the direction of the arrow 92 as was described previously for the embodiments of FIGS. 6 and 7, thereby moving the links 84 and 85 past their said singular position and towards the configuration shown with dotted lines in FIG. 11. The at least one pre-tensioned tension springs 72 will then rapidly engage the braking elements 51 and the resulting braking forces will begin to decelerate the assembly of the mass element 52 and braking elements 51 and thereby the components 53 that are to be tested.

The brake engagement and disengagement mechanism of FIG. 11 has a number of advantages. Firstly, it adds minimal weight to the braking elements 51. Secondly, it requires relatively small amount of force (to be exerted by the cable 91) to engage the brake. Thirdly, since the linkage (links links 84 and 85) has to be displaced a relatively small distance to engage the brake, the time taken to engage the brake is also very short.

In the embodiments of FIGS. 2, 4 and 5, the mechanical shock testing machines, to increase structural rigidity of the machines, it is generally desirable to provide a relatively rigid structure 94 similar to the base structure 24 to bridge the top ends of the rails 22 to keep them from relative deflection.

In the embodiments of FIGS. 2, 4 and 5 the mechanical shock testing machines are shown to be vertically installed. The advantage of installing the machines vertically is that gravity is also used for downward acceleration of the mass elements. However, if relatively high deceleration levels with significantly longer durations are desired to be achieved, then the total length of travel of the machine mass element becomes too long to make a vertical machine practical. For example, for a deceleration level of 4,000 G and duration of ten milliseconds, the mass element and braking element assembly of the embodiment of FIG. 5 have to travel about two meters only during the pulse duration. Thus, considering the considerable travel that is required to accelerate the mass element assembly to the required velocities and the safety margins that have to be provided, it becomes clear that the total length of the required rails will be too long to make vertical installation practical. For these reasons, when relatively high deceleration pulses and long pulse durations are required, then horizontal installment becomes the only practical option.

It will be, however, appreciated by those skilled in the art that when using relatively long rails over which a carriage (in this case a mass element such as the mass element 52 with the attached braking elements 51) is to travel, then the rail has to be supported along its length, at least at several points. This means that the carriage bearing has to have at least a section of it open to allow travel over the rail supports. Thus, round rails such as the rails 22 of the embodiments 2, 4 and 5 and their corresponding braking elements (29 in FIGS. 3A and 3B and 51 in FIG. 6), cannot be used. In such mechanical shock testing machines, rails of different cross-sectional areas may be used. The rail supports may be continuous or be provided at certain intervals along the length of the rail. In general, the designs can be provided with continuous rail supports to eliminate vertical deflection of the rail between supports which would cause the mass element (carriage) assembly to be subjected to an undesirable up and down and possibly lateral oscillatory motion disturbances with high frequency content. Such motion disturbances may significantly affect the shock testing results, particularly since in addition to the resulting unwanted up and down and lateral acceleration/deceleration loading of the components that are being tested; they would also cause the applied braking forces to vary during the applied deceleration pulses.

Figure 12:
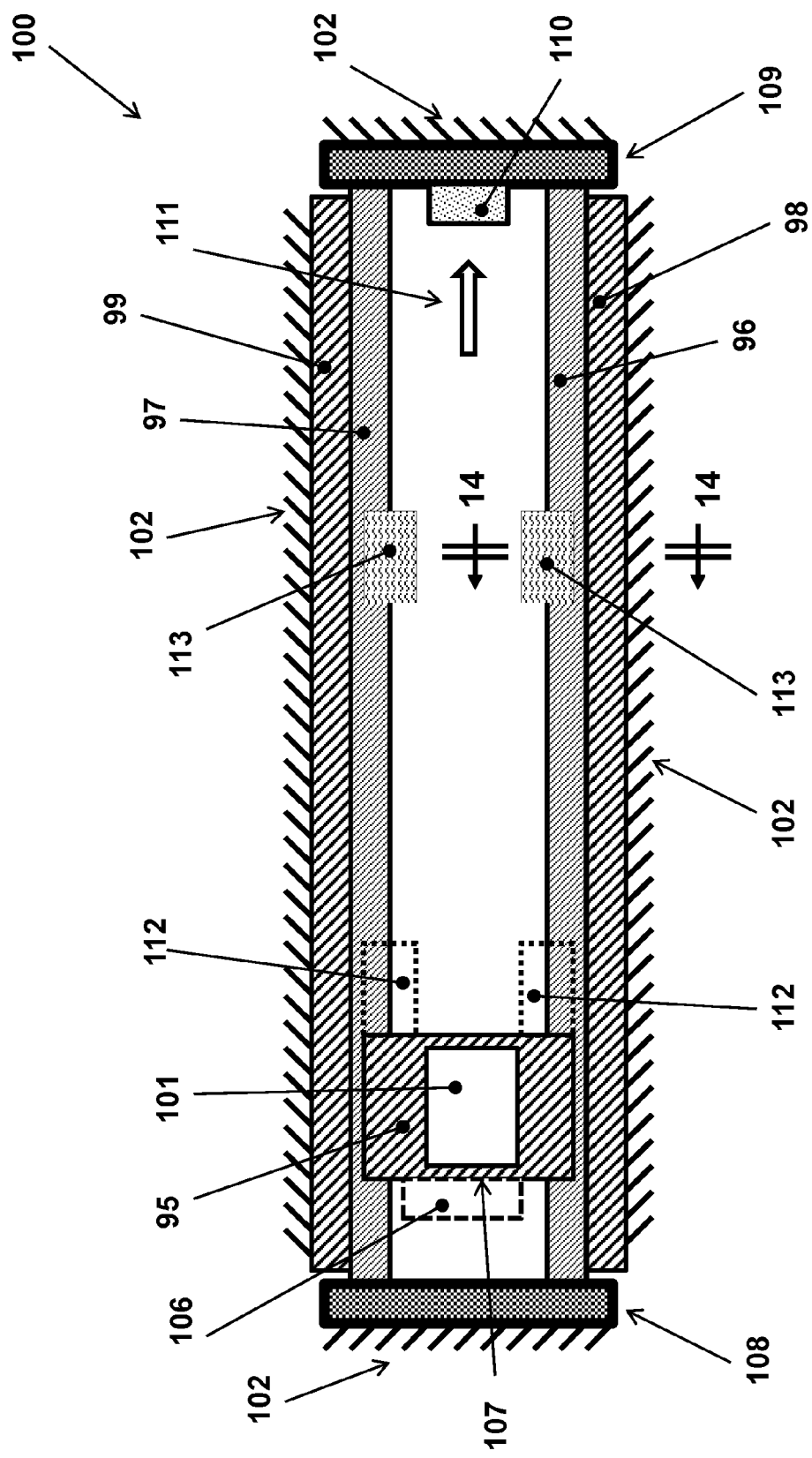
FIG. 12 illustrates the schematic of the third embodiment of the mechanical shock testing machine.

The schematic of the third embodiment 100 of the mechanical shock testing machine is shown in FIG. 12. The shock testing machine 100 is horizontally installed e.g., so that it could accommodate relatively long rails as was described above. The rails 96 and 97 are attached to the machine structure 102 (only shown as ground) by rigid support structures 98 and 99, which are more clearly shown in the cross-sectional view of FIG. 14. The rails 96 and 97 can be provided with relatively rigid end structures 108 and 109. A mass element 95 is provided with sleeve bearings 103 and 104 as shown in the cross-sectional view of FIG. 14 to travel along the rails 96 and 97 freely with minimal friction. Considering that the mass element 95 is accelerated from close to its left-most position as shown in FIG. 12 using one of the aforementioned methods described for the embodiments of FIGS. 2, 4 and 5, a proper shock absorber 110 is provided on the rigid support structure 109 in case that the braking elements to be described below fail to bring the mass element 95 as it travels in the direction of the arrow 111 during a shock testing event.

The braking elements 113 of the embodiment 100 of the mechanical shock testing machine may be configured as the embodiment 30 of FIG. 2 in which the braking elements (29 in FIG. 2) are normally engaged and positioned downstream for the mass element (23 in FIG. 2) to engage at a prescribed velocity. In the schematic of the embodiment 100 of FIG. 12, similar and already engaged braking elements 113 are shown as similarly positioned at a certain distance from the indicated initial position of the mass element 95. Embodiments of the braking element 113 design are described below.

Alternatively, the braking elements 112 (shown in dotted lines) of the embodiment 100 of the mechanical shock testing machine may be configured as the embodiment 50 of FIG. 5 in which the braking elements (51 in FIG. 5) are initially disengaged and attached to the mass element (52 in FIG. 5) and is engaged once the mass element has gained a prescribed velocity. In the schematic of the embodiment 100 of FIG. 12, similar (disengaged) braking elements 112 (in dotted lines) are shown as similarly attached to the mass element 95. Embodiments of the braking element 112 design are described below.

Figure 13:
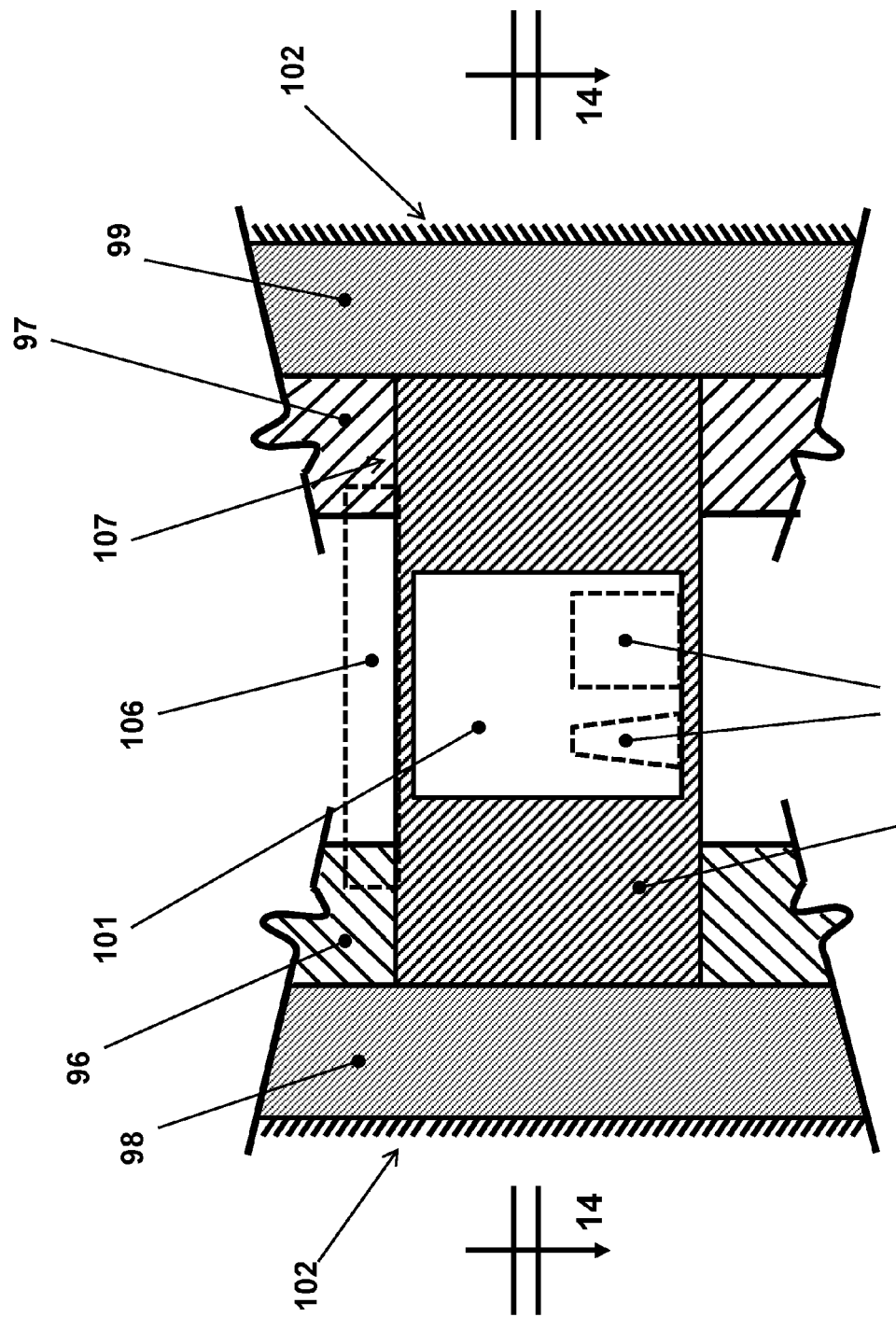
FIG. 13 illustrates the schematic of the top view of the third embodiment of the mechanical shock testing machine showing the mass element, rails and their support structure in which the rails are horizontally installed.
Figure 14:
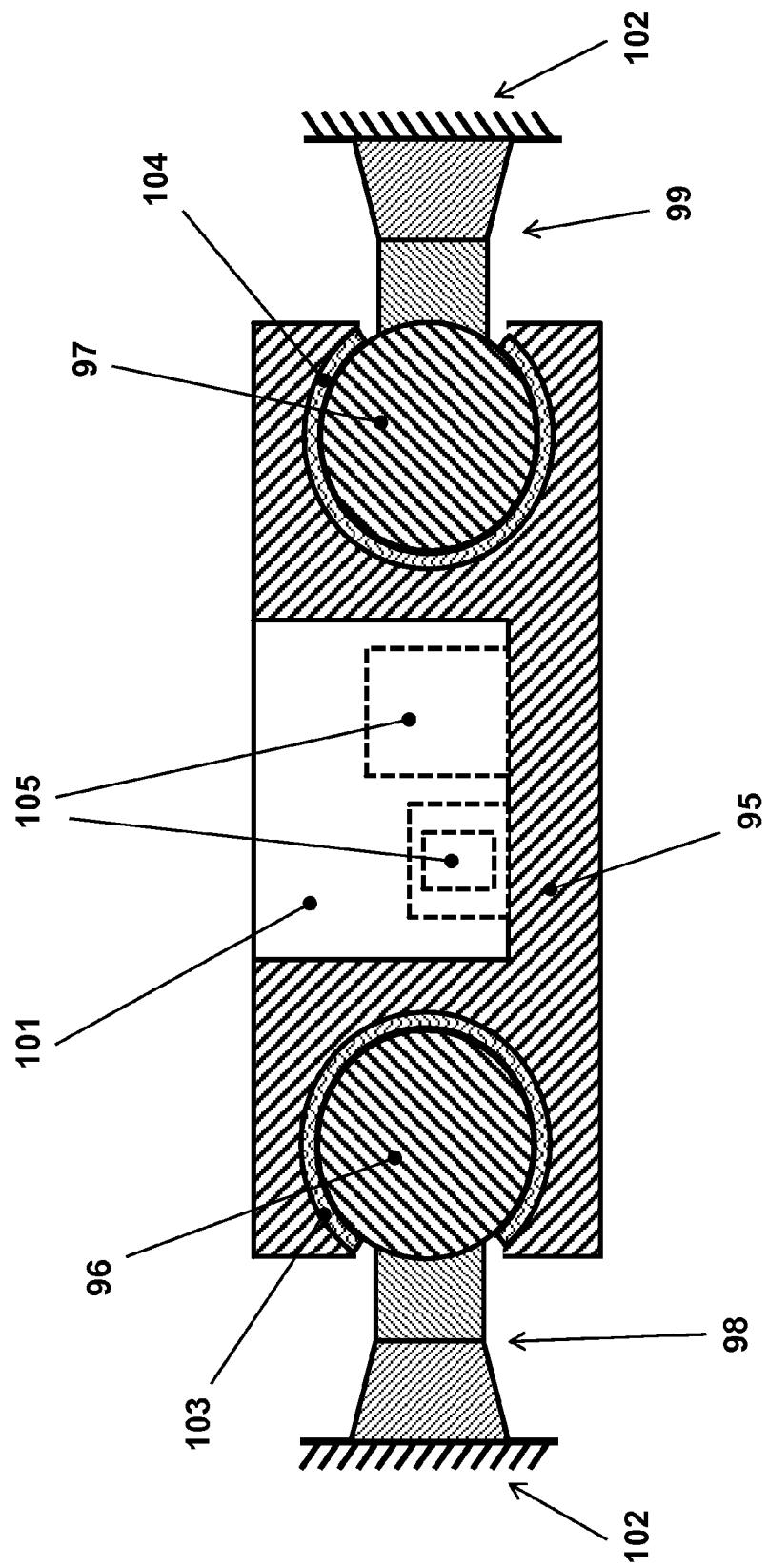
FIG. 14 illustrates the schematic of cross-sectional view 14-14 of the horizontally installed mechanical shock testing machine of the embodiment shown in the top view of FIG. 13.

The top view of a section of the third embodiment 100 of the mechanical shock testing machine is shown in FIG. 13. FIG. 13 shows the top view of a section showing the mass element 95 of the mechanical shock testing machine 100 and its rails 96 and 97 over which it travels. As can be seen in the cross-section 14-14 of FIG. 13 which is shown in FIG. 14, the mass element 95 rides over the rails 96 and 97 with the provided bearing sleeves 103 and 104, respectively. The rails 96 and 97 are attached to the machine structure 102 (not shown) by support structures 98 and 99, respectively. The support structures 98 and 99 can be made out of solid steel or stainless steel to be very rigid. The machine structure 102 is can also be made out of heavy structural steel and can be firmly attached to a concrete slab to withstand the testing shock loading with negligible vibration.

As can be seen in the cross-sectional view of FIG. 14, the rail bearings are positioned in the mass element 95 such that the center of mass of the mass element 95 is positioned essentially in the plane of long axes of the rails 96 and 97 so that as the mass element is being subjected to the shock testing deceleration pulse, the mass element would not tend to tip over. In addition, the mass element 95 is provided with a pocket 101 for positioning the components 105 (FIGS. 13 and 14) which are being tested as close as possible to the center of mass of the mass element 95. However, if a testing component 106 is too large to fit the pocket 101, then it may be mounted over the surface 107 of the mass element 95 as shown in FIGS. 12 and 13.

Figure 15:
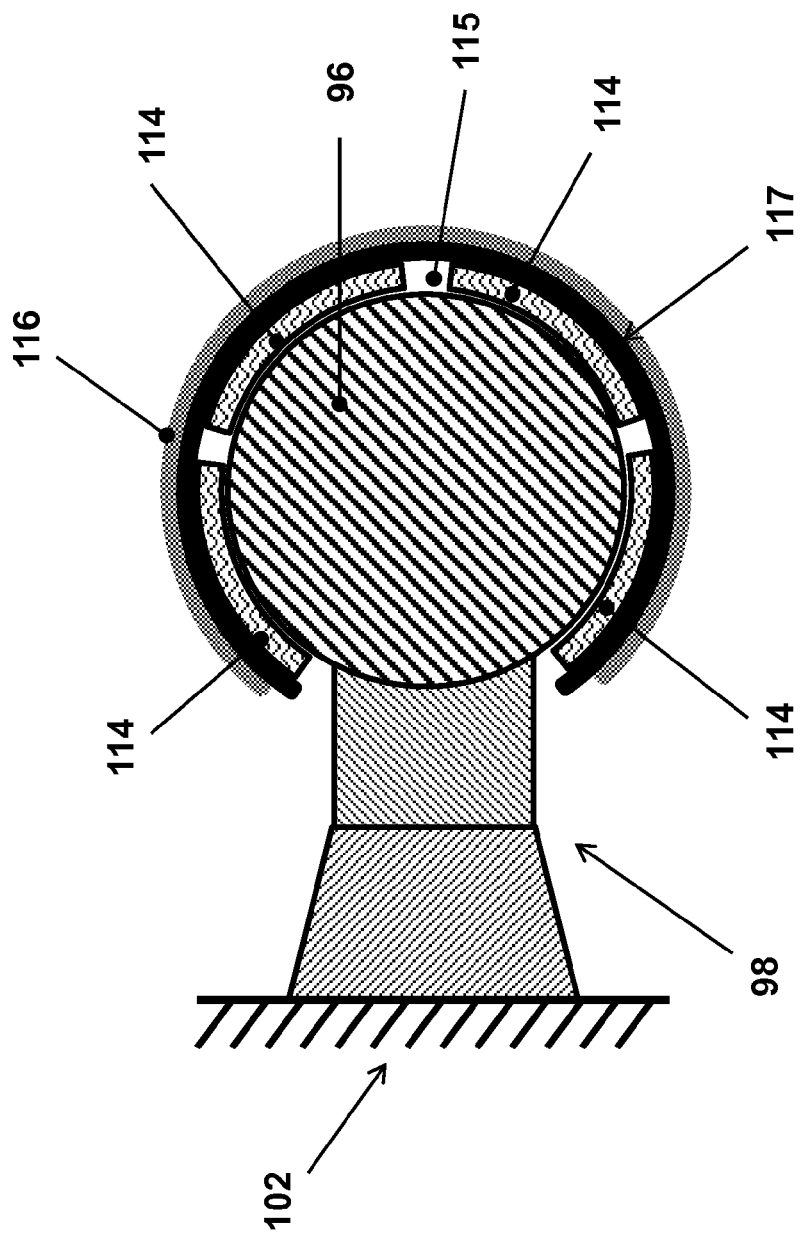
FIG. 15 illustrates a cross-sectional view of one possible design of the braking element of the third embodiment of the mechanical shock testing machine of FIG. 12.

A cross-sectional view taken along line 14-14 in FIG. 12 of the braking elements 113 is shown in the schematic of FIG. 15. The braking elements 113 are very similar to the braking elements 29 of the mechanical shock testing machine embodiment 30 of FIG. 2, except that the braking elements 113 have to accommodate the rail 96 support structure 98 (99 for the rail 97). As can be seen in FIG. 15, the braking elements 113 are similarly provided with several braking pad segments 114 (in the schematic of FIG. 15, four braking pad segments) that are in close contact with the surface of the rail 96. Gaps 115 can be provided between the braking pad segments 114 to minimize their interference during testing (as they slide down the rail 96) as well as while adjusting the braking pads 114 pressure on the surface of the rail 96 as will be described later in this disclosure. In general, since most braking pad materials are relatively soft and fragile, they are provided with relatively strong and stiff backing plates (collectively indicated as the braking pads 114) to ensure relatively uniform distribution of the applied braking pressure as will be described below. Alternatively, the braking pad materials may be attached to a single "C" shaped sleeve 117 (such as being made out of thin spring material) as shown in FIG. 15.

It will be appreciated by those skilled in the art that numerous methods may be used to apply pressure to the braking pad segments 114 against the surface of the rails 96 and 97 to generate the desired braking forces. However, as was previously discussed, it is highly desirable for the braking elements 113 to be as lightweight as possible to minimize the aforementioned impulsive impact forces generated as the mass element 95 comes into contact with the braking elements 113 as was described for the embodiment 30 of FIG. 2. For these reasons, the means of applying pressure to the braking pad segments 114 must also be lightweight and allow for easy adjustment of the braking forces, i.e., the pressure between the braking pads 114 and the surfaces of the rails 96 and 97. A very simple such lightweight means for applying pressure to the braking pads 114 is the use of at least one "C" shaped spring element 116 (similar to the elements 65 in FIG. 6), which is/are preloaded to apply the desired level of compressive force to the braking pad segments 114 to achieve the desired level of pressure between the braking pads and the surfaces of the rails 96 and 97, thereby to achieve the desired braking element 113 forces. The advantages of using the at least one "C" shaped spring element 116 include design simplicity and capability of using several of them along the length of the braking pads 114 to achieve a relatively uniform distribution of braking forces. In addition, by using several such "C" shaped spring elements 116 with different levels of preloading levels, almost any braking force level can be obtained with the accuracy levels that are expected for shock testing.

In another embodiment of the braking elements 113, the forces to be applied to the braking pad segments 114 of the braking elements 113 (FIG. 12) to generate the desired braking forces are provided using certain means such as those that will be described using the schematics of FIGS. 16 and 17.

Figure 16:
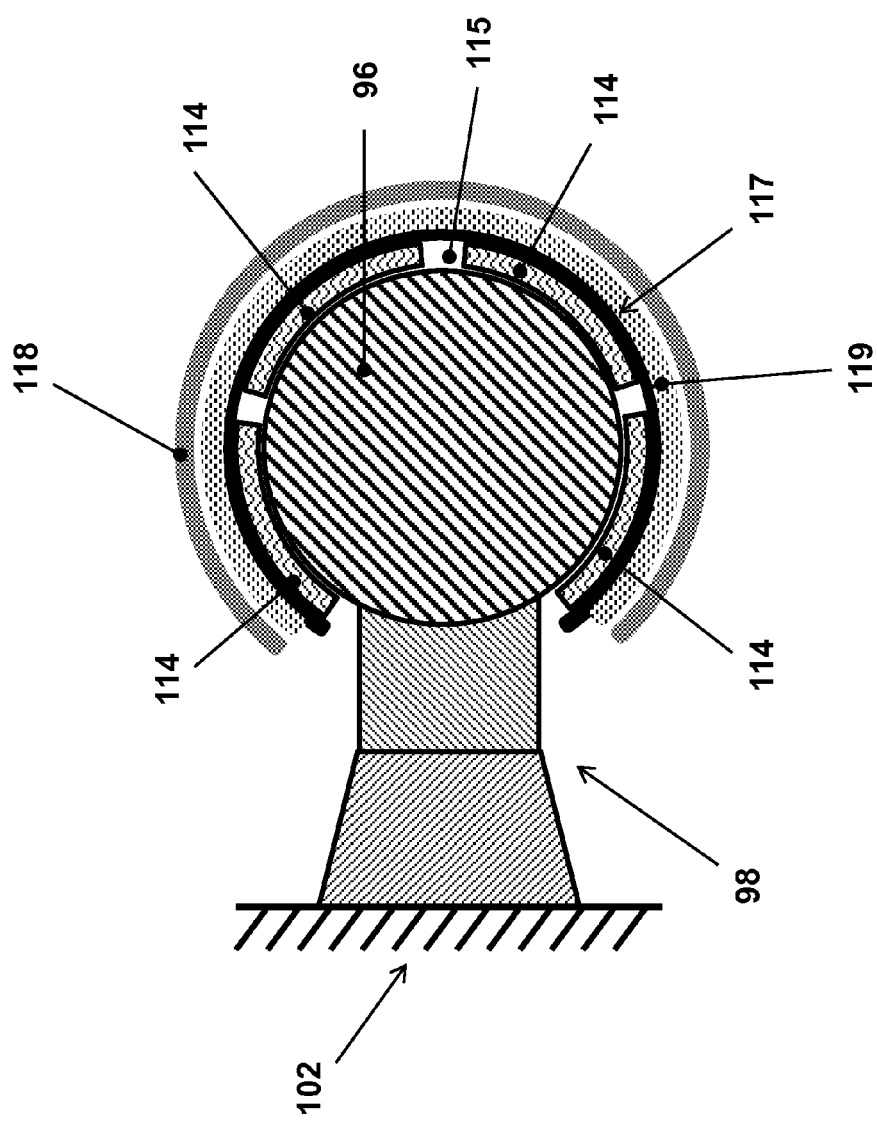
FIG. 16 illustrates a cross-sectional view of another possible design of the braking element of the third embodiment of the mechanical shock testing machine of FIG. 12.

In these embodiments of the braking elements 113, as can for example be seen in the schematic of FIG. 16, all components of the braking elements are the same as those of the embodiment of FIG. 15, except the following. Firstly, the at least one "C" shaped spring elements 116 can be eliminated. And secondly, the braking pad segments 114 materials are provided with the backing "C" shaped sleeve 117 as was previously discussed. The "C" shaped sleeve 117 can be made out of relatively thin and easily bending spring plate that would provide minimal resistance to externally applied pressure in the direction of pressing the braking pad segments 114 against the surfaces of the rails 96 and 97, FIGS. 12 and 15. In this embodiment, the braking elements 113 are provided with a relatively "rigid" and "C" shaped structure 118, which can cover most of the surface of the backing "C" shaped sleeve 117 as shown in FIG. 16. The "C" shaped structure 118 can be lightweight but strong and can also be stiff and is used as a structure for applying force to the braking pad segments 114 via the "C" shaped sleeve 117. It will be appreciated by those skilled in the art that numerous methods and means can be used for this purpose. Several such methods and means are described below, noting that it is highly desirable for such method to provide lightweight means with readily adjustable force level capability. It will, however, be appreciated by those skilled in the art that other methods and means known in the art may also be used for this purpose.

In one embodiment, so-called pneumatic bags 119 (similar to pneumatic lifting bags or blood pressure measurement cuffs), commonly constructed with thin and flexible material with relatively inextensible layers are positioned between the "C" shaped sleeves 117 and the relatively rigid "C" shaped structure 118 as shown in FIG. 16. Then by pressurizing the pneumatic bags 119 through a one way valve, for example similar to those used in basketballs or those used for tires (not shown) to an appropriate level, the desired level of pressure is applied to the braking pad segments 114 via the "C" shaped sleeve 117. Advantages of using such pneumatic pressure bags 119 are their wide availability; being very lightweight; ease of pressure and thereby braking force adjustment; ease of assembly with the braking elements 113; and low cost.

Figure 17:
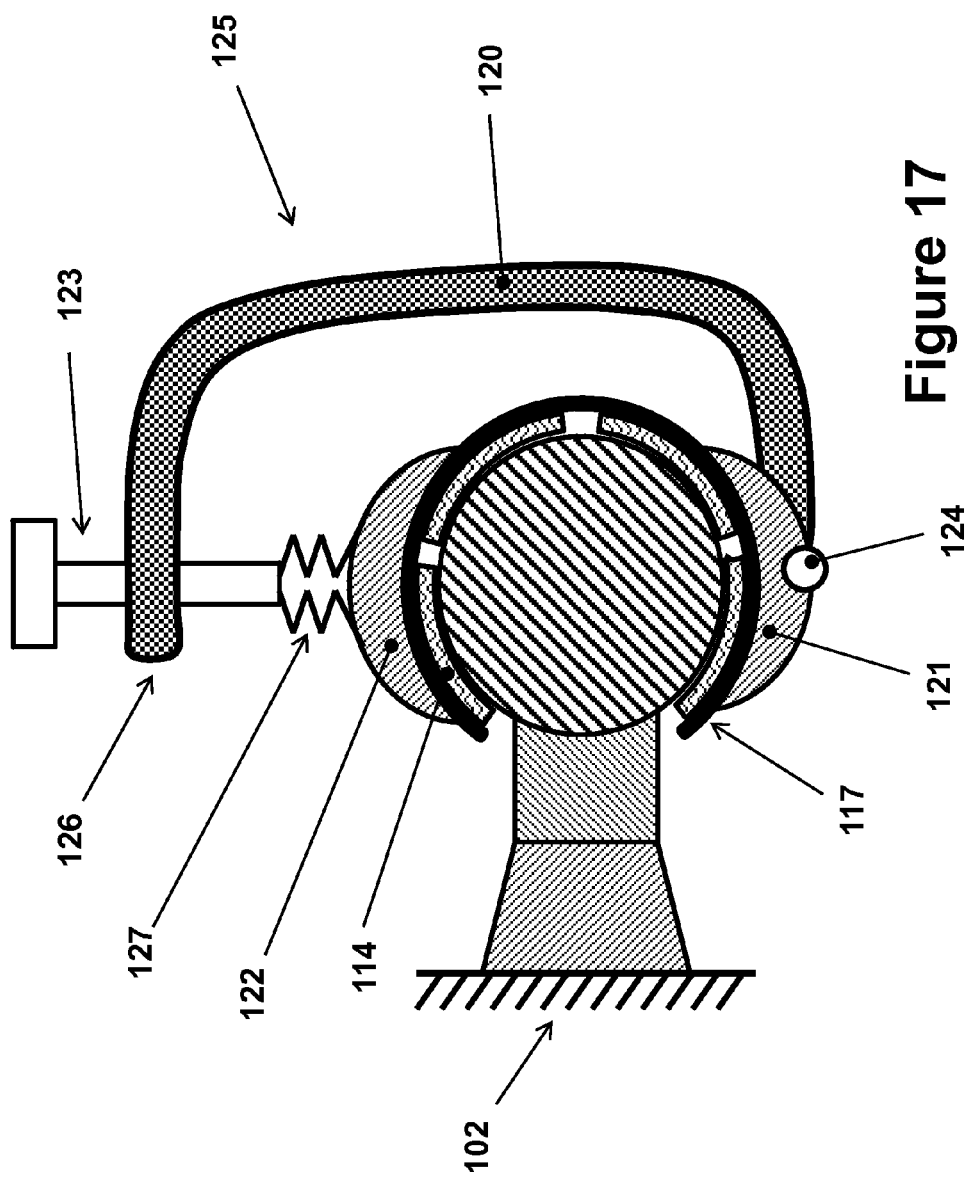
FIG. 17 illustrates a cross-sectional view of another possible design of the braking element of the third embodiment of the mechanical shock testing machine of FIG. 12.

In another embodiment shown in the schematic of FIG. 17, the braking forces are generated by the braking elements 113 by compressive forces generated using a "C" clamp 125. The "C" clamp 125 uses the "C" shaped structure 120 to apply compressive force to the braking pad segments 114 via the "C" shaped sleeve 117. The "C" clamp 125 is provided with the end element 121 on one end, which has curved surfaces to closely engage the "C" shaped sleeve 117 of the braking pad segments 114 as shown in FIG. 17. A relatively thin layer of rubber or the like lining material (not shown) can be placed on the contacting surfaces of the end element 121 to ensure that the applied compressive forces are properly distributed over the contacting surface of the "C" shaped sleeve 117. The end element 121 can be attached to the "C" shaped structure 120 of the "C" clamp 125 by a ball joint 124 to minimize the required efforts for proper positioning of the "C" clamp over the braking elements 113. On the opposite end 126 of the "C" shaped structure 120 of the "C" clamp 125, a tightening bolt 123 is provided that is threaded to the end 126 of the "C" shaped structure 120 which is used to apply compressive force to the "C" shaped sleeve 117 via the element 122. Similar to the end element 121, the element 122 can also be made with curved surfaces to closely engage the "C" shaped sleeve 117 of the braking pad segments 114 as shown in FIG. 17. A relatively stiff spring 127, such as those made with a set of Belleville washers, can be positioned between the bolt 123 and the element 122 to facilitate compressive force level adjustment. A relatively thin layer of rubber or the like lining material (not shown) can also be placed on the contacting surfaces of the end element 122 to ensure that the applied compressive forces are properly distributed over the contacting surface of the "C" shaped sleeve 117.

In the embodiments 30, 50 and 100 of FIGS. 2, 5 and 12, respectively, rails with circular cross-sections were shown to be used. In the construction of these embodiments, particularly since these mechanical shock testing machines are intended to be used in tests in which the mass elements (23, 52 and 95 in the embodiments 30, 50 and 100 of FIGS. 2, 5 and 12) are required to gain very high velocities prior to impact, then the bearings to be used in the mass elements are sleeve type bearings designed for high speed operation such as "Black Racer Ceramic Coated Linear Bearings" available from Daemar USA, Inc of Atlanta, Ga. Such bearings are available as full cylindrical sleeves for embodiments 30 and 50 of FIGS. 2 and 5 as well as sectional sleeves for the embodiment 100 of FIG. 12.

It will, however, be appreciated by those skilled in the art that if either of the mechanical shock testing machine embodiments 30, 50 or 100 of FIGS. 2, 5 and 12, respectively, is designed for tests in which their corresponding mass elements are not required to gain very high speeds, then one may use ball bushing type of bearings in the construction of their mass elements (23, 52 and 95 in the embodiments 30, 50 and 100 of FIGS. 2, 5 and 12). Such ball bushings are well known in the art and are widely available in the commercial market.

In the embodiments 30, 50 and 100 of FIGS. 2, 5 and 12, respectively, rails with circular cross-sections were shown to be used. It will, however, be appreciated by those skilled in the art that rails with other cross-section types may also be used. In general, however, when the mass elements (23, 52 and 95 in the embodiments 30, 50 and 100 of FIGS. 2, 5 and 12) are required to gain very high speeds, the rails are desired to be designed to constrain all possible motions of the mass elements except their translational motion along the long axis of the rail as the rails with circular cross-sections used in the embodiments 30, 50 and 100 of FIGS. 2, 5 and 12, respectively, are designed to do. Such motion constraining mechanisms are generally required since the mass elements are desired to be lightweight and thereby prone to lateral motions during the target braking element impact (e.g., embodiment 30 of FIG. 2) or braking engagement (e.g., embodiment 50 of FIG. 5).

The operation of the mechanical shock testing embodiment 100 of FIG. 12 that is equipped with the braking elements 113 with either one of the "normally engaged" embodiments of FIGS. 15-17 or the like as described above. In such mechanical shock testing machines, the mass element 95 engages the braking elements 113 at certain prescribed velocity to provide the desired deceleration pulse (shock loading) to the components being tested as was previously described for the embodiment 30 of FIG. 2.

An alternative embodiment of the mechanical shock testing machine 100 uses the braking elements 112, FIG. 12, which are fixedly attached to the mass element 95—similar to the braking elements 51 of the embodiment 50 of FIG. 5 which are fixedly attached to the mass element 52. In this embodiment of the mechanical shock testing machine, the braking elements 112 are initially not engaged, i.e., they do not resist motion of the mass element 95 along the rails 96 and 97 by exerting braking forces. As a result, the assembly of the mass element 95 and braking elements 112 can be accelerated along the rails 96 and 97 without braking force resistance using one or more of the aforementioned means such as pre-tensioned bungee cords or pneumatic cylinders or other similar means as was previously described to gain a predetermined velocity, noting that the means of accelerating the mass element 95 can be an appropriate number of appropriately sized and pre-tensioned bungee cords. Then once the mass element and braking element assembly has gained the predetermined velocity, the braking elements 112 are engaged and begin to apply a prescribed level of braking force to the rails 96 and 97, thereby causing the mass element 95 to be decelerated at the desired rate, thereby subjecting the testing components 105, FIGS. 13 and 14, to a predetermined and essentially constant deceleration (shock) pulse that lasts until the assembly of the mass element 95 and braking elements 112 come to rest as was previously described for the embodiment 50 of FIG. 5. The methods of designing and constructing the braking elements 112 and mechanisms for their activation once the mass element 95 has gained the prescribed velocity are described below.

Figure 20:
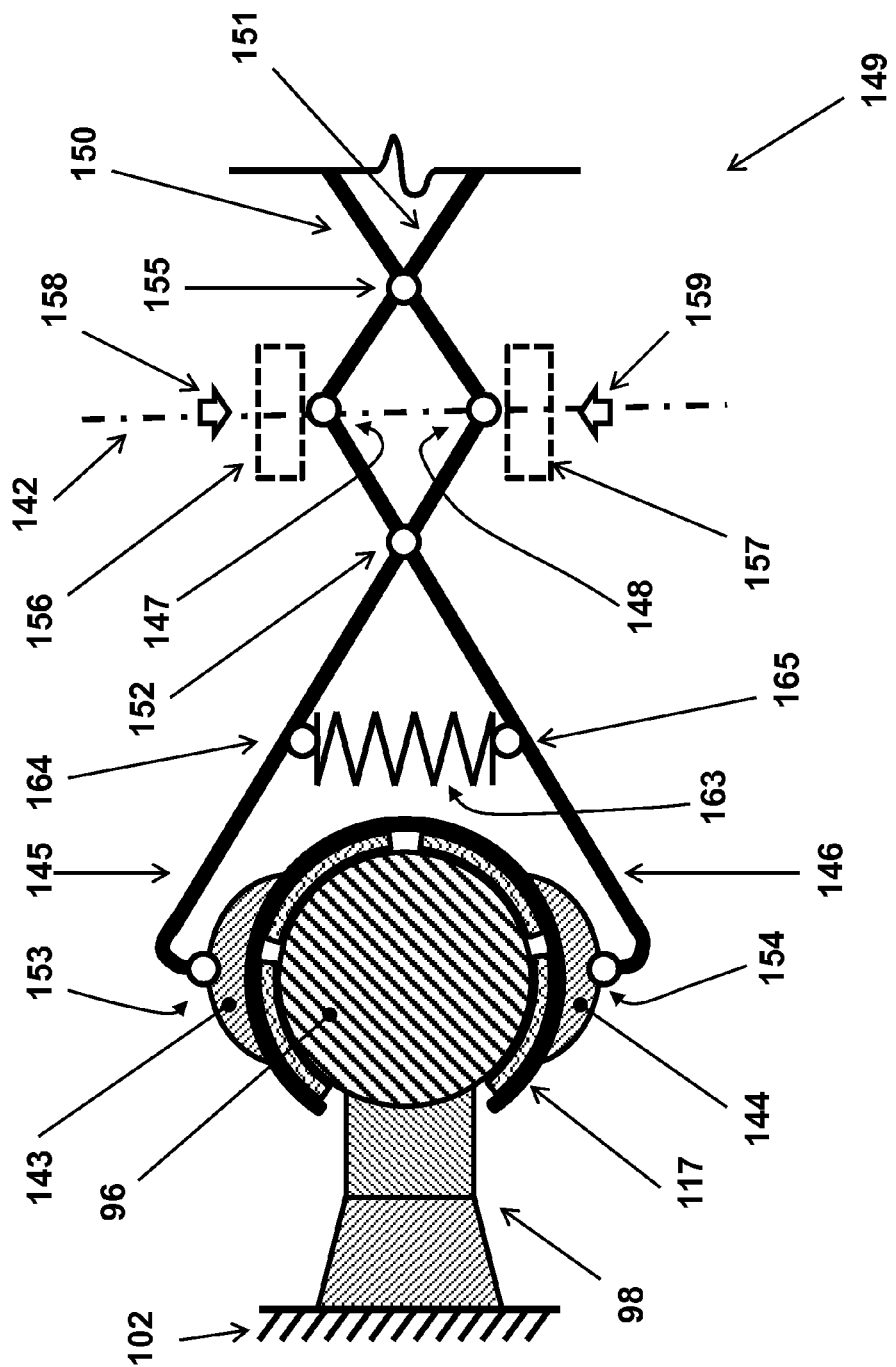
FIG. 20 illustrates a cross-sectional view of another possible design of the braking element of the third embodiment of the mechanical shock testing machine of FIG. 12 with the braking elements attached to the mass element of the machine.

In one embodiment of the mechanical shock testing machine 100 which uses the braking elements 112, FIG. 12, which are fixedly attached to the mass element 95 is shown in the schematic of FIG. 20. FIG. 20 illustrates half the cross-sectional view through the braking element 112, noting that the full view is symmetrical about the indicated centerline 142. All the components of the brake elements are as shown in FIG. 15 (without the at least one "C" shaped spring element 116). The relatively rigid elements 143 and 144 are attached to the braking pad backing "C" shaped sleeve 117 as shown in FIG. 20. A double scissor shaped linkage mechanism 149 is then used to keep each braking element 112 disengaged for free travel over each rail 96, 97 and engage it when the mass element 95 has gained its desired speed as described below.

The aforementioned double scissor shaped linkage mechanism 149 is constructed with two pairs of links 145 and 146 on the illustrated half of the cross-sectional view of FIG. 20 and symmetrically positioned pair of links 150 and 151 for the opposite half of the cross-sectional view of FIG. 20. The pair of links 145 and 146 and the opposing pair of links 150 and 151 are hinged together with the pin joints 152 and 155, respectively. The pair of links 145 and 146 are attached to the relatively rigid elements 143 and 144 with the pin joints 153 and 154, respectively, on one end, and to the opposing pair of links 150 and 151 with the pin joints 147 and 148 on the other end (pin joint 147 connecting the links 146 and 151 and the pin joint 148 connecting the links 145 and 150), as shown in FIG. 20. The links 150 and 151 are similarly attached to the elements of the braking element 112 on the rail 97, FIG. 12.

In its engaged configuration, the brake pads 114 of the braking elements 112 are pressing against the surfaces of the rails 96 and 97, FIGS. 12, 15 and 20. The brake pad pressure can be provided by preloading at least one "C" shaped spring element 116 (not shown) as was described for the embodiment of FIG. 15; and/or the pneumatic bags 119 (not shown) with the backing relatively stiff "C" shaped structure 118 as shown for the embodiment of FIG. 16; and/or with at least one pre-tensioned tensile springs 163 which is attached to the links 145 and 146 with the pins 164 and 165, respectively, as shown in FIG. 20; or other similar means. The pressure of the brake pads 114 over the surfaces of the rails 96 and 97 is adjusted as described for the embodiments of FIGS. 15 and 16 and for the case of the at least one pre-tensioned tensile springs 163 by selecting the proper number, spring rate and length of the springs.

Figure 21:
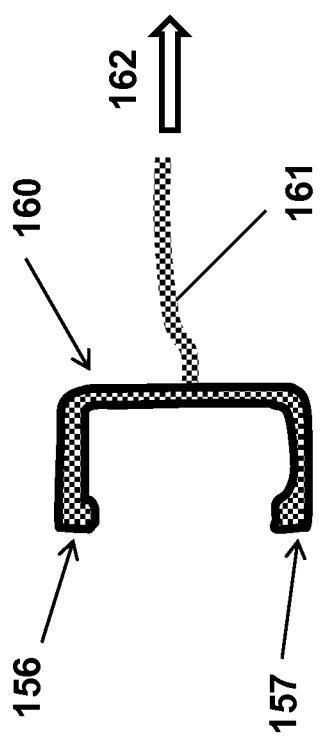
FIG. 21 illustrates the schematic of the brake release element for the brake embodiment of FIG. 20 of the mechanical shock testing machine of FIG. 12.

In the disengaged configuration, the tips 156 and 157 of a relatively rigid U-shaped element 160 shown in FIG. 21 are used to keep the joint 147 joining the links 146 and 151 and the joint 148 joining the links 145 and 150 at a required distance to relieve pressure of the brake pads 114 over the surfaces of the rails 96 and 97, thereby disengaging the braking element 112 and allowing free travel of the mass element 95 along the rails. It will be appreciated by those skilled in the art that the process of disengaging the braking elements 112 requires the application of compressive pressure in the direction of the arrows 158 and 159 to overcome the aforementioned forces generated by one or more of the aforementioned means to generate braking pressures, followed by the insertion of the tips 156 and 157 of the U-shaped "holder element 160 over the joints 147 and 148 to keep the braking elements 112 in their disengaged state.

A cable 161 is also attached to the relatively rigid U-shaped element 160 as can be seen in FIG. 21. The free end of the cable 161 is then attached to the structure 102 of the mechanical shock testing machine embodiment 100 of FIG. 12. Then similar to the previously described embodiment 50 of FIG. 5, the length of the cable 161 is adjusted so that as the mass element 95 is accelerated along the rails 96 and 97 using one of the aforementioned means and once it has attained a desired velocity, then the cable 161 is similarly pulled to dislodge the U-shaped "holder element 160, thereby causing the braking elements 112 to be engaged.

It will be appreciated by those skilled in the art that other means such as pneumatic cylinders that are pressurized to an appropriate level (not shown) may also be used to generate the desired brake pad pressures. Such pneumatic means may be used in many applications since their pressure can be readily adjusted to the desired level and also since they provide near constant compressive force (against the links 145 and 146 to tend to bring them closer to each other, thereby generating the desired braking forces) due to their required small range of displacements. For the latter reasons, such pneumatic cylinders do not require permanent connection to a source of pressurized gas. Such a pneumatic cylinder may be configured and pressurized as was previously described for the pneumatic cylinder 67 of the embodiment of FIG. 8 to keep the joints 147 and 148 at the required distance to disengage the braking elements 112. A cable similar to the cable 61 of FIG. 8 is then attached to the structure 102 of the mechanical shock testing machine embodiment 100 of FIG. 12 to similarly open the valve 70 and release the cylinder pressure once the mass element 95 as attained a desired velocity, thereby causing the braking elements 112 to be engaged.

Figure 23:
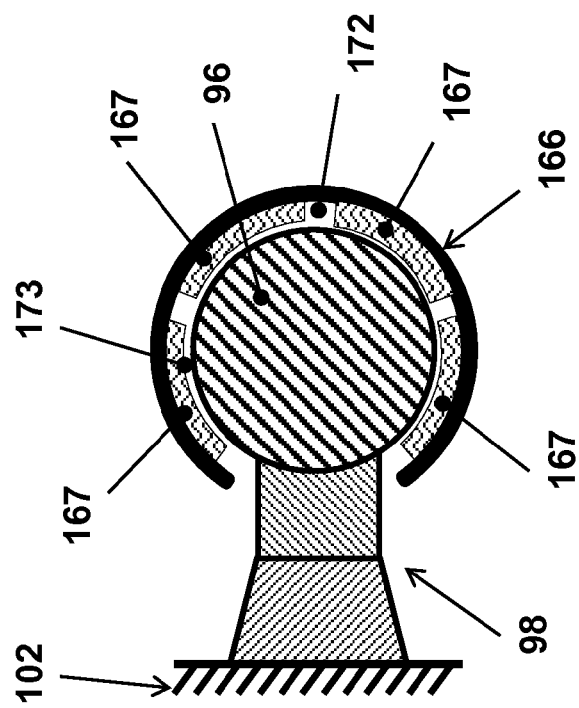
FIG. 23 illustrates a cross-sectional view of the brake assembly section of one of the rails of the brake engagement mechanism of the embodiment of FIG. 22.

Another embodiment of the engagement mechanism for the braking elements 112 is shown in the schematic of FIG. 22. In FIG. 22, a longitudinal cross-sectional view of one of the braking elements 112 is shown together with a portion of the rail around which brake engagement occurs. The braking elements 112 are shown to be constructed with relatively rigid brake housings 166, which are attached to the mass element 95. The at least one braking pads 167 are then fixedly attached to the inside of the brake housing 166 as shown the schematic of the cross-sectional view 23-23 of FIG. 23 of the braking element 112 (FIG. 22). Gaps 172 may be provided between the braking pads 167 to prevent their interference during braking operation as well as for ease of replacement. As can be seen in FIGS. 22 and 23, a gap 173 is provided between the braking pads 167 and the surface of the rails (rail 96 in FIG. 22) while the mass element 95 and its attached braking elements 112 are beyond the sleeves 169, which are fixedly attached symmetrically to the rails 96 and 97, as shown in FIG. 22. In the indicated positioning of the mass element 95 and braking elements 112, the assembly can travel freely along the rails 96 and 97.

Figure 24:
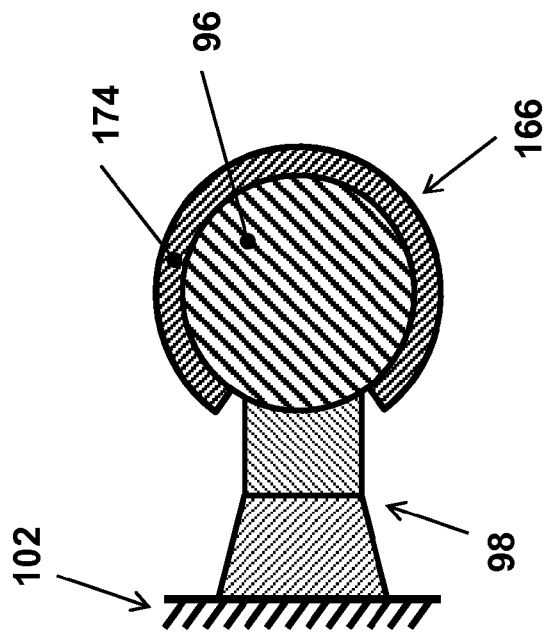
FIG. 24 illustrates a cross-sectional view of the provided sleeves over the mechanical shock testing machine rails to engage the braking pads under pressure to generate the desired mass element decelerating braking force.

The cross-sectional view 24-24, FIG. 22, shown in the schematic of FIG. 24 shows the positioning of the sleeve 169 over the rail 96 and similarly over the rail 97. The sleeves 169 are provided with tapered ends 170 on the approaching side of the mass element 95 and braking elements 112 assembly as shown in FIG. 22. The braking pads 167 are provided with appropriate thickness to fill the gap 168, while the backing structure 166 provides enough elasticity to achieve a prescribed braking force once the braking pads have engaged the sleeves 169. Then as the mass element and braking element assembly is accelerated to a prescribed velocity in the direction of the arrow 111 in FIG. 12 and arrow 171 in FIG. 22, noting that the sleeves 169 are positioned downstream, such as resting against the end structure 109, then as the braking pads 167 engage the sleeves 169, a prescribed level of pressure is generated between the braking pads 167 and the outer surface of the sleeves 169. The resulting braking forces will then decelerate the mass element 95 and braking elements 112 assembly at a predetermined rate, thereby subjecting the testing components attached to the mass element 95 to the same deceleration event.

As can be seen in FIG. 22, the sleeves 169 are provided with tapered ends 170 on the approaching side of the mass element 95 and braking elements 112 assembly to provide the means for smooth and gradual engagement of the braking pads 167 with the outer surfaces of the sleeves 169. The sleeves 169 can be provided with smooth and very hard surfaces to minimize wear and achieve relatively constant braking pressure (force) as the mass element 95 and braking elements 112 assembly is decelerated.

As it will be appreciated by those skilled in the art that the brake engagement mechanism illustrated in the schematics of FIGS. 22-24 also require a means of adjusting the braking forces once the brakes are engaged. In this embodiment, the method of adjusting the braking forces, i.e., adjusting the induced braking pressure once the braking elements 112 are engaged as described above can be by adjusting the gap 168 between the braking pads 167 and the rails 96 and 97.

One method of adjusting the gap 168 is by placing shims with appropriate thickness between the brake pads 167 and the backing structure 166. Such a design requires that the brake pads 167 be attached to the backing structure by a fastener via separate backing plates (not shown) such as those commonly used in disc brakes in cars. Shearing pins may also be required between the separate backing plates and the backing structure 166 (not shown) for high braking forces.

An alternative method of adjusting the braking forces once the brake elements 112 have engaged is by varying the stiffness of the backing structure 166 in resisting the reaction forces to the pressure applied by the brake pads 167 onto the surfaces of the raids 96 and 97. It will be appreciated by those skilled in the art that such reaction forces would tend to "open up" the end of the "C" shaped backing structure 166. The stiffness of the "C" shaped backing structure can then be varied by any one of the previously described methods such as by the addition of "C" shaped spring elements 116 of the embodiment of FIG. 15 (such as with no or minimal preload) with appropriate stiffness; or external clamps similar to the "C" clamp 125 shown in FIG. 17 but without the preloaded springs 127, with appropriate stiffness, which may also be directly connected snugly with positioning pins to provided protrusions on the backing structure 166 (not shown); or by placing pressure preloaded compressive gas springs between the positioning pins to provided protrusions on the backing structure 166; or other well known means in the art.

It will be appreciated by those skilled in the art that when using the sleeves 169 to engage the brake pads 167 as shown in FIG. 22, the bearings 103 and 104 that ride on the surface of the rails 96 and 97 must accommodate the increased diameter of the outer surface of the sleeves 169, FIG. 14. This can be accomplished simply by constructing each of the bearings 103 and 104 in longitudinal sections (similar to the brake pads 114 in FIG. 15), each with proper backing springs to form two or more spring loaded bearing shoes. The springs can be nearly constant force springs and can deflect an appropriate amount to accommodate the diameter of the sleeves 169.

In the schematic of FIG. 22, the rails 96 (and 97) are shown to be provided with separate sleeves 169 to engage the brake pads 167. It will, however, be appreciated by those skilled in the art that the sleeves 169 and its tapered portions 170 may be integral to the rails 96 and 97. However, since the sleeve sections are more prone to wear, the section of the rail comprising of the sleeves 169 and its tapered portions 170 can be constructed as separate units and are each attached to the support structures 98 and 99 and can be aligned through centering holes and steps on either sides.

In an alternative embodiment of the mechanical shock testing machine 100 of FIG. 12, the braking pads can be attached directly to the mass element 95 and would engage a provided contact surfaces which are mounted onto the structure of the machine 102 to generate the desired braking force. In general, the braking pads may be of any shape, but flat pads are can be used since they are easy to fabricate and shape. The corresponding brake contact surfaces, which must run parallel to the rails 96 and 97, can also consist of flat surfaces which are significantly easier to fabricate, align and maintain.

It will be appreciated by those skilled in the art that numerous such design geometries are possible for such mass element attached brake pad machine designs. In the following, two such basic design geometries that utilize planar (flat) brake pads and mating contact surfaces are described. It will however be appreciated by those skilled in the art that many other planar and/or non-planar brake pad geometries with their corresponding mating contact surfaces may also be readily designed and that the presentation of the following two examples is not intended to exclude other designs with planar and/or non-planar geometries. Planar pads are, in general, highly advantageous since they do not change shape as they wear; they are very easy to fabricate; their pressure can be easily adjusted by simple means; and they can be readily replaced. Such mass element attached brake pad machine designs can be implemented on both basic embodiments 30 (50) and 100 of FIGS. 2 (5) and 12, respectively.

Figure 25:
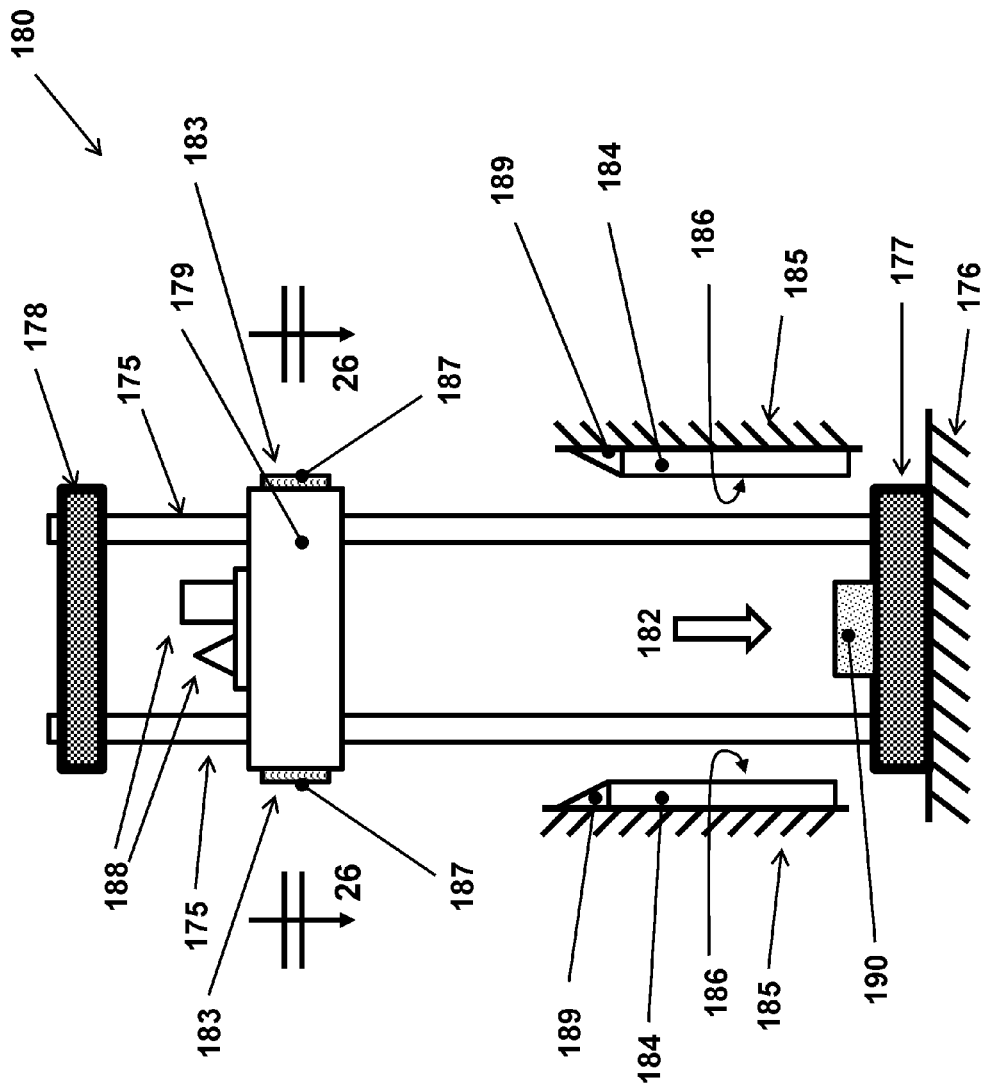
FIG. 25 illustrates the schematic of the fourth embodiment of the mechanical shock testing machine.

The schematic of a fourth embodiment 180 of the mechanical shock testing machine is shown in FIG. 25. The mechanical shock testing machine 180 may be installed either vertically or horizontally or be oriented in any arbitrary orientation. The rails 175 are attached to rigid support structures 177 and 178. When the machine 180 is installed vertically as shown in FIG. 25, the support structure 177 can be fixed to a relatively massive foundation 176. When horizontally (non-vertically) installed, both supports structures 177 and 178 can be grounded but the support structure 177 may still be used to be fixed to a relatively massive foundation 176. As was indicated for the embodiments 30 and 50 of FIGS. 2 and 5, unlike the embodiment 100 of FIG. 12, this design has a practical limitation on the length of the rails. A mass element 179 is provided with sleeve bearings 181 as shown in the cross-sectional view 26-26 of FIG. 26. The bearing sleeves 181 are selected to allow free travel of the mass element 179 along the rails 175 with minimal friction. In the schematic of FIG. 25, the mass element 179 is considered to be accelerated from close to its top-most position in the direction of the arrow using one of the aforementioned methods described for the embodiments of FIGS. 2, 4 and 5 to the desired velocity prior to deceleration via the engagement of the system brakes as described below.

In the embodiment 180 of FIG. 25, the brake pads 183 are firmly attached to the mass element 179. The brake pads 183 can be positioned symmetrically with respect to the rails 175 and the mass element 179 can be similarly symmetrical shaped relative to the rails 175 to minimize the level of rocking forces and moments that can be generated during the mass element acceleration as well as deceleration. The embodiment 180 is also provided with brake engaging elements 184 which are firmly attached to the structure 185 (not fully shown) of the mechanical shock testing machine 180. The flat surface portions 186 of the brake engaging elements 184 are positioned parallel to the outside surfaces 187 of the brake pads 183, FIG. 25. Then as the mass element 179 is accelerated in the direction of the arrow 182, at a prescribed velocity, it would enter the space between the brake engagement elements 184, at which time the surfaces 187 of the brake pads 183 engage the surfaces 186 of the brake engaging elements 184, thereby applying braking forces to the mass element 179 to cause the 1 mass element to decelerate as was previously described, thereby applying the generated deceleration to the testing components 188, which are firmly attached to the mass element 179, FIG. 25.

In an embodiment of the mechanical shock testing machine 180, the brake pads 183 can be attached to the mass element 179 with relatively stiff springs (such as Belleville washers) placed between their backing plates and the surface of the mass element (not shown). Then by adjusting the spring preloads and the positioning of the surfaces 186 of the brake engaging elements 184 relative to the surfaces 187 of the brake pads 183, the pressure exerted by the braking pads 183 to the surfaces of the brake engaging elements 184 and thereby the level of braking force and thereby the deceleration rate of the mass element can be varied as was previously described, for example for the embodiment 50 of FIG. 5. In addition, the brake engaging elements 184 can be provided with initial tapered regions 189 to allow for a smooth application of the braking forces to the mass element 179.

In general, a proper shock absorber 190, FIG. 25, is provided on the rigid support structure 177 in case that the braking elements fail to decelerate the mass element 179 to a stop.

Figure 26:
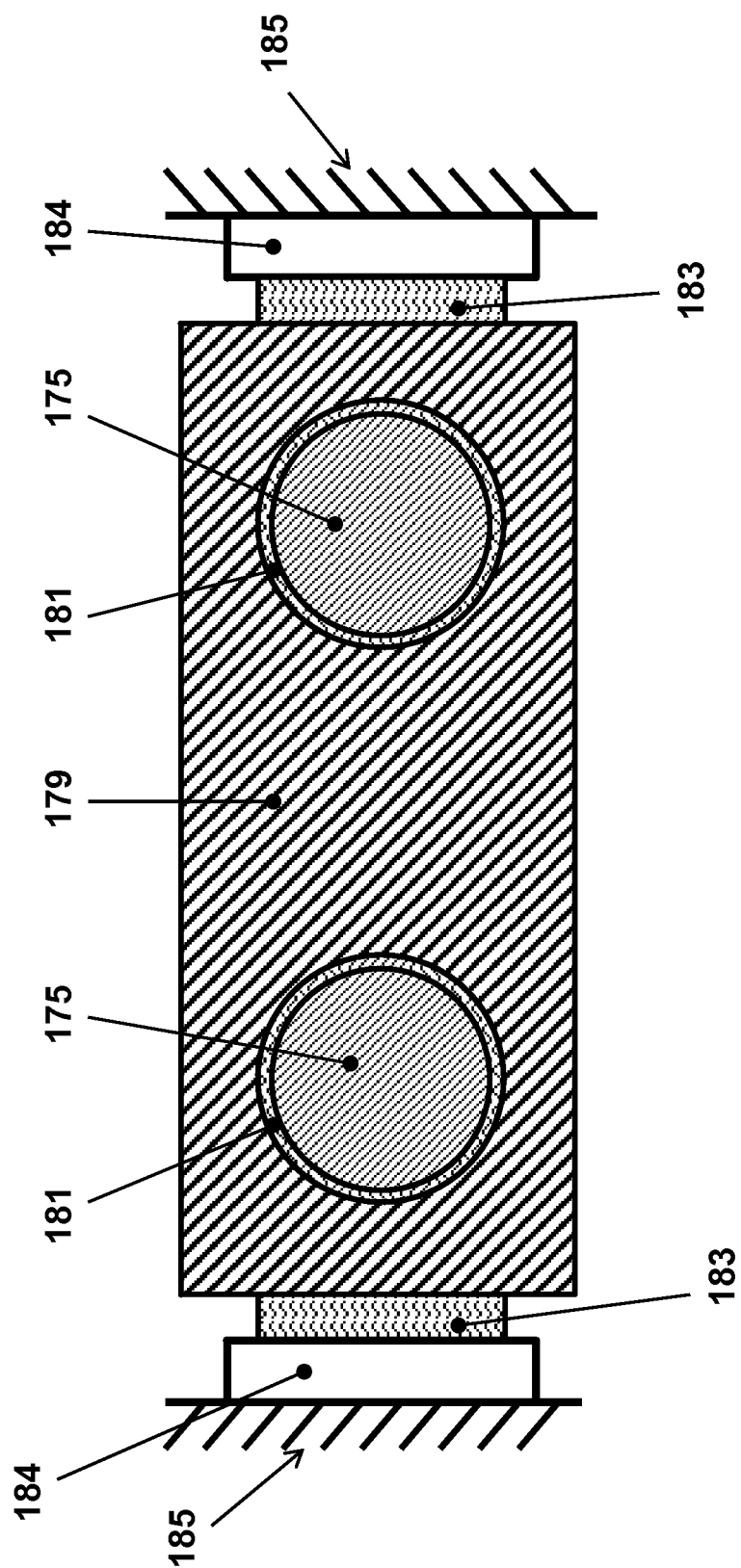
FIG. 26 illustrates cross-sectional view 25-25 of the mechanical shock testing machine embodiment of FIG. 25.
Figure 27:
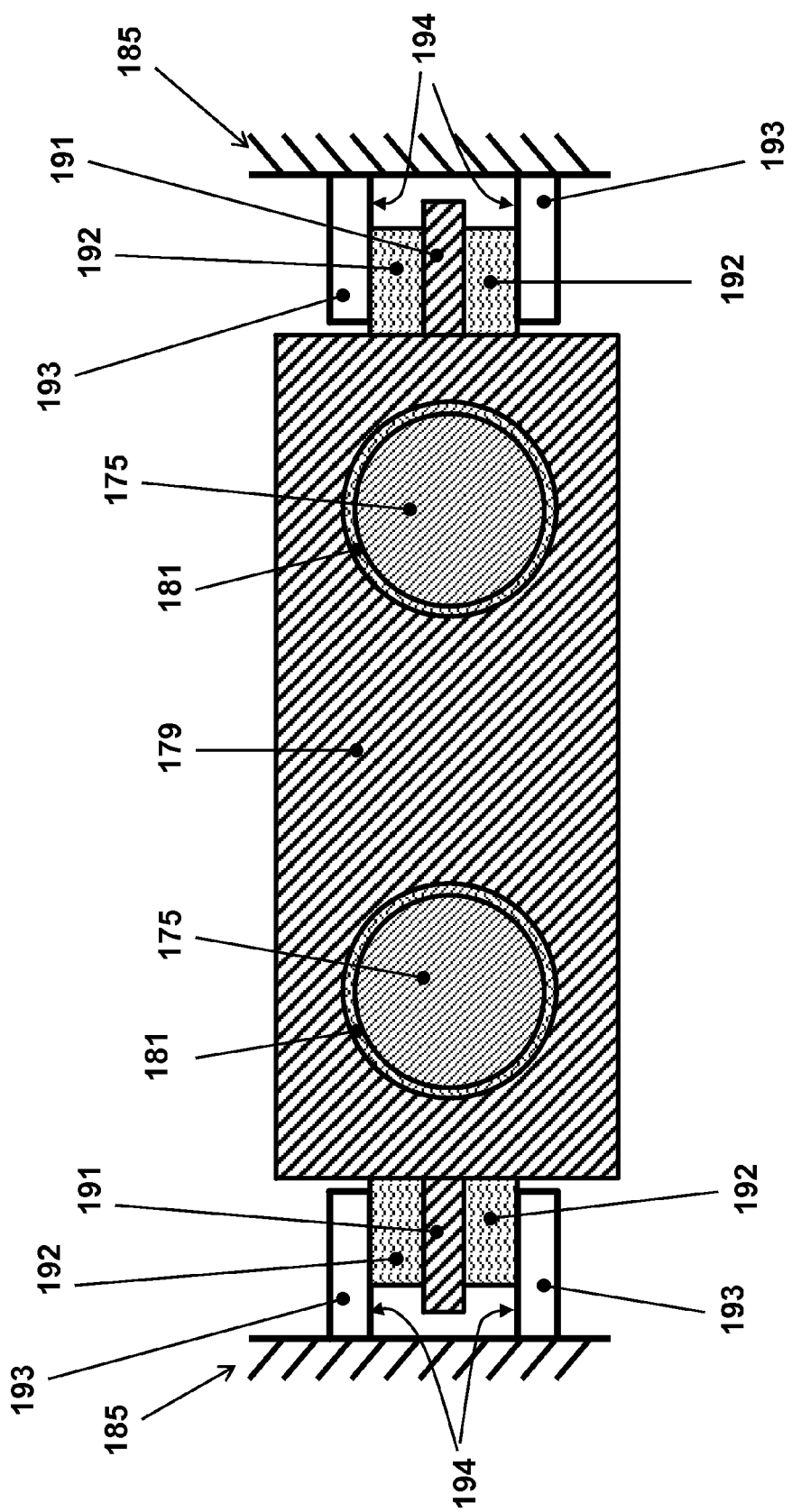
FIG. 27 illustrates the cross-sectional view 25-25 of the alternative design of the mechanical shock testing machine embodiment of FIG. 25.

In an alternative embodiment 180 of the mechanical shock testing machine of FIG. 25, pairs of braking pads are used on each side of the mass element 179 (not shown in FIG. 25). With this design, the cross-sectional view 27-27 is as shown in the schematic of FIG. 27. In the cross-sectional view of FIG. 27, the mass element 179, rails 175, sleeve bearing 181 and the machine structure 185 are identical to those shown in the cross-sectional view of FIG. 26 and the embodiment 180 of FIG. 25. In this alternative design of the embodiment 180 of the mechanical shock testing machine, the mass element 179 is provided with the symmetrical "flanges" 191 on its both sides to the sides of which the brake pads 192 are attached. The brake pads 192 can be almost as long as the height of the mass element 179 while slightly clearing the top and bottom edges of the mass element. The mechanical shock testing machine can also be provided with the brake pad engaging plates 193, FIG. 27, which are fixedly attached to the rigid structure 185 of the machine. In this alternative design of the mechanical shock testing machine embodiment 180 shown in FIG. 25, the brake engaging elements 184 are replaced by the brake engaging plates 193 at similar locations close to the machine end structure 177. As can be observed, the brake engaging plates 193 form "U-shape" channels with proper opening so that their inner surfaces 194 would engage both brake pads 192 on both sides of the mass element 179.

Then as the mass element 179 is accelerated in the direction of the arrow 182, FIG. 25, at a prescribed velocity the two pairs of brake pads 192 on each side of the mass element 179 will enter the "U-shape" channels formed by the brake engaging plates 193, thereby causing the braking mechanism of the machine to be engaged, thereby applying braking forces to the mass element 179 and cause the mass element to decelerate as was previously described, thereby applying the generated deceleration to the testing components 188, which are firmly attached to the mass element 179, FIG. 25.

In an embodiment of the above alternative design of the mechanical shock testing machine embodiment 180, the brake pads 192 can be attached to the "flanges" 191 of the mass element 179 with relatively stiff springs (such as Belleville washers) placed between their backing plates and the surface of the "flanges" 191 (not shown). Then by adjusting the spring preloads and the positioning of the surfaces 194 of the brake engaging plates 193, the pressure exerted by the braking pads 192 to the surfaces of the "U-shape" channels of the brake engaging plates 193 and thereby the level of braking force and thereby the deceleration rate of the mass element can be varied as was previously described, for example for the embodiment 50 of FIG. 5. In addition, the brake engaging elements 193 can be provided with similar initial tapered regions (not shown) to allow for a smooth application of the braking forces to the mass element 179.

Figure 28:
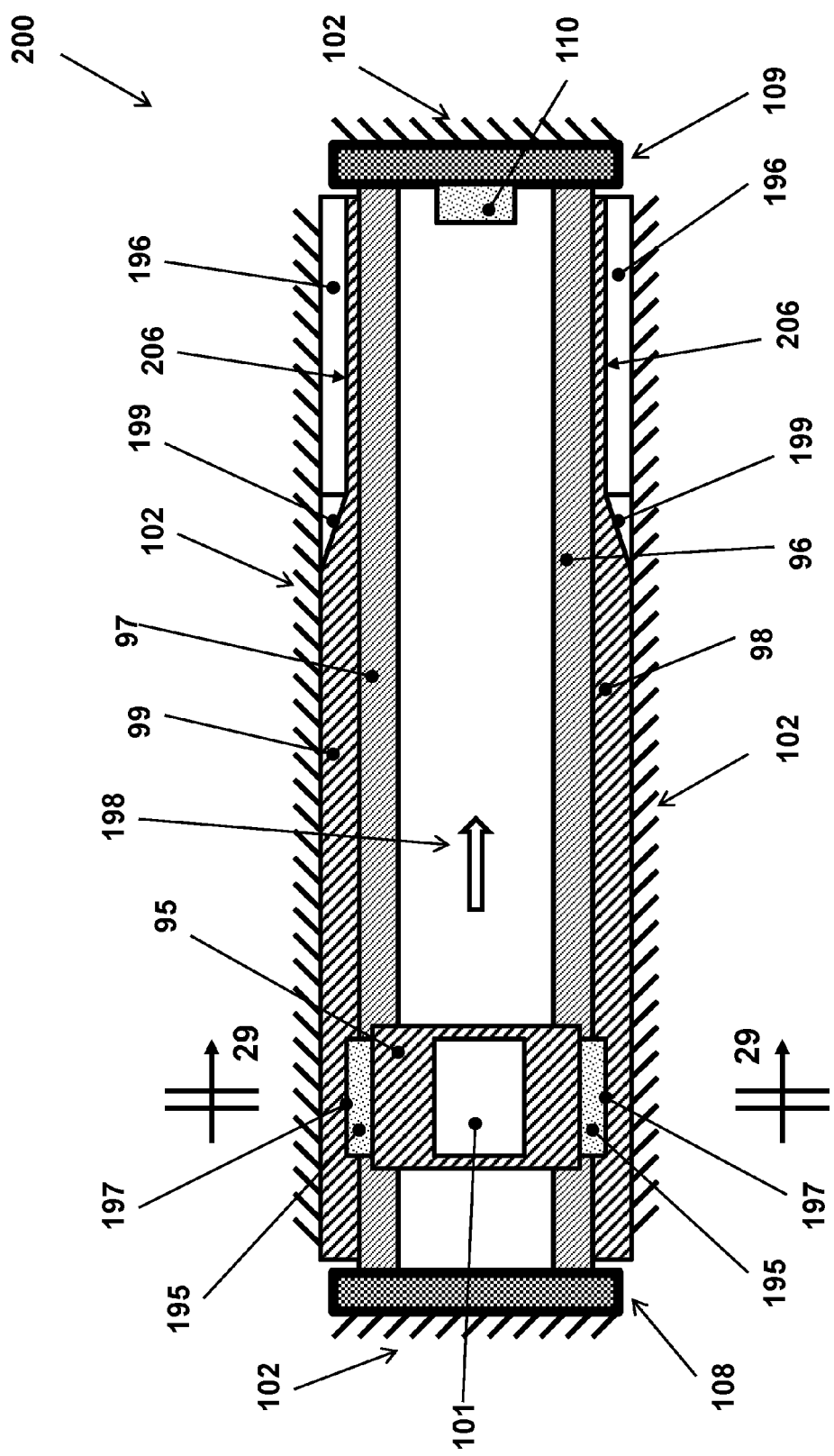
FIG. 28 illustrates the cross-sectional view of the fifth embodiment of the mechanical shock testing machine of the present invention designed based on the third embodiment of the mechanical shock testing machine of FIG. 12.
Figure 29:
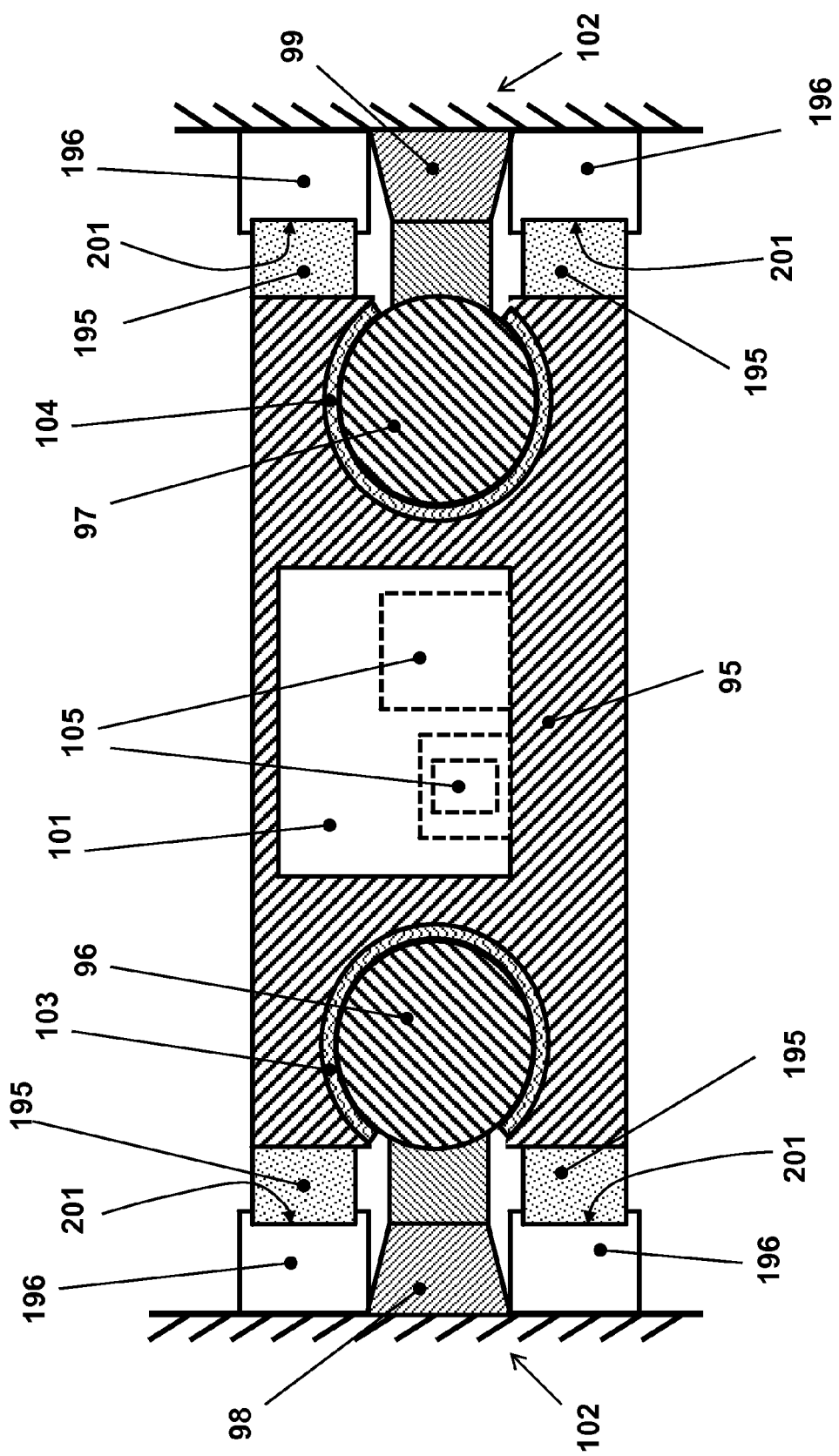
FIG. 29 illustrates cross-sectional view 28-28 across the mass element of the mechanical shock testing machine embodiment of FIG. 28.

The above embodiment 180 of FIG. 25 was a modification of the embodiment 50 of FIG. 5. In a similar manner, the embodiment 100 of FIG. 12 with the braking elements 112 can be modified by providing the brake pads on its mass element and the mating braking surfaces attached to the machine structure. The schematic of the resulting fifth embodiment 200 of the mechanical shock testing machine is shown in FIG. 28. In the schematic of FIGS. 28 and 29, all members that are not enumerated are identical to those of the embodiment 100 of FIG. 12. A cross-sectional view 29-29, FIG. 29, across the mass element 95 is shown in FIG. 29.

The mechanical shock testing machine 200 can be installed horizontally so that there is minimal limitation on the length of its rails 96 and 97 and thereby the range of travel of the mass element 95.

In the embodiment 200 of FIG. 28, the brake pads 195 are firmly attached to the mass element 95. The brake pads 195 can be positioned symmetrically with respect to the rails 96 and 97 as shown in the cross-sectional view of FIG. 29. The embodiment 200 is also provided with brake engaging elements 196, FIGS. 28 and 29, which are firmly attached the structure 102 (not fully shown) of the mechanical shock testing machine 200. The flat surfaces 201 of the brake engaging elements 196, FIG. 29, are positioned parallel to the outside surfaces 197 of the brake pads 195, FIG. 28. Then as the mass element 95 is accelerated in the direction of the arrow 198, at a prescribed velocity, it would enter the space between the brake engaging elements 196, at which time the surfaces 197 of the brake pads 195 engages the surfaces 201 of the brake engaging elements 196, thereby applying braking forces to the mass element 95 and cause the mass element to decelerate as was previously described, thereby applying the generated deceleration to the testing components 105, which are firmly attached to the mass element 95, as was described for the embodiment 100 of FIG. 12.

In an embodiment of the mechanical shock testing machine 200, the brake pads 195 are attached to the mass element 95 with relatively stiff springs (such as Belleville washers) placed between their backing plates and the surface of the mass element (not shown). Then by adjusting the spring preloads and the positioning of the surfaces 200 of the brake engaging elements 196 relative to the surfaces 197 of the brake pads 195, the pressure exerted by the braking pads 195 to the surfaces of the brake engaging elements 196 and thereby the level of braking force and thereby the deceleration rate of the mass element can be varied as was previously described, for example for the embodiment 50 of FIG. 5. In addition, the brake engaging elements 196 can be provided with initial tapered regions 199, FIG. 28, to allow for a smooth application of the braking forces to the mass element 95.

It will be appreciated by those skilled in the art that for the braking mechanism embodiments of FIG. 22; FIGS. 25 and 26; FIGS. 25 and 27; and FIGS. 28 and 29, the braking pad must be adjusted such that they come into contact with their corresponding brake engaging elements essentially at the same time. The braking forces provided by the braking pads on each side of the machine mass element are also highly desirable to be essentially at the same levels so that the machine mass element is subjected to minimal tipping and twisting forces and moments. The latter requirement, however, necessitates setting of the braking force levels on each side of the mass elements separately. However, it will be appreciated by those skilled in the art that since friction forces are very difficult to accurately control and they usually vary significantly by environmental effects and wear and it is difficult to very accurately measure, therefore one should expect certain level of difference between the braking forces that in practice will be applied to each side of the mass element. The sleeve bearings of the mass elements must therefore be designed to handle such differences in the braking forces on each side of the mass element.

Therefore, the braking mechanism of the mechanical shock testing machines embodiments of FIG. 22; FIGS. 25 and 26; FIGS. 25 and 27; and FIGS. 28 and 29 may be provided with means to equalize the braking pad pressure on either side of the related mass elements to minimize the difference between the resulting braking forces on either side of the mass elements. In the above embodiments of the present mechanical shock testing machines, this can be achieved by linking the brake pads on both sides of the mass elements and via preloaded compressive springs as described below for the braking mechanism of the embodiment 200 of FIGS. 28 and 29.

Figure 30:
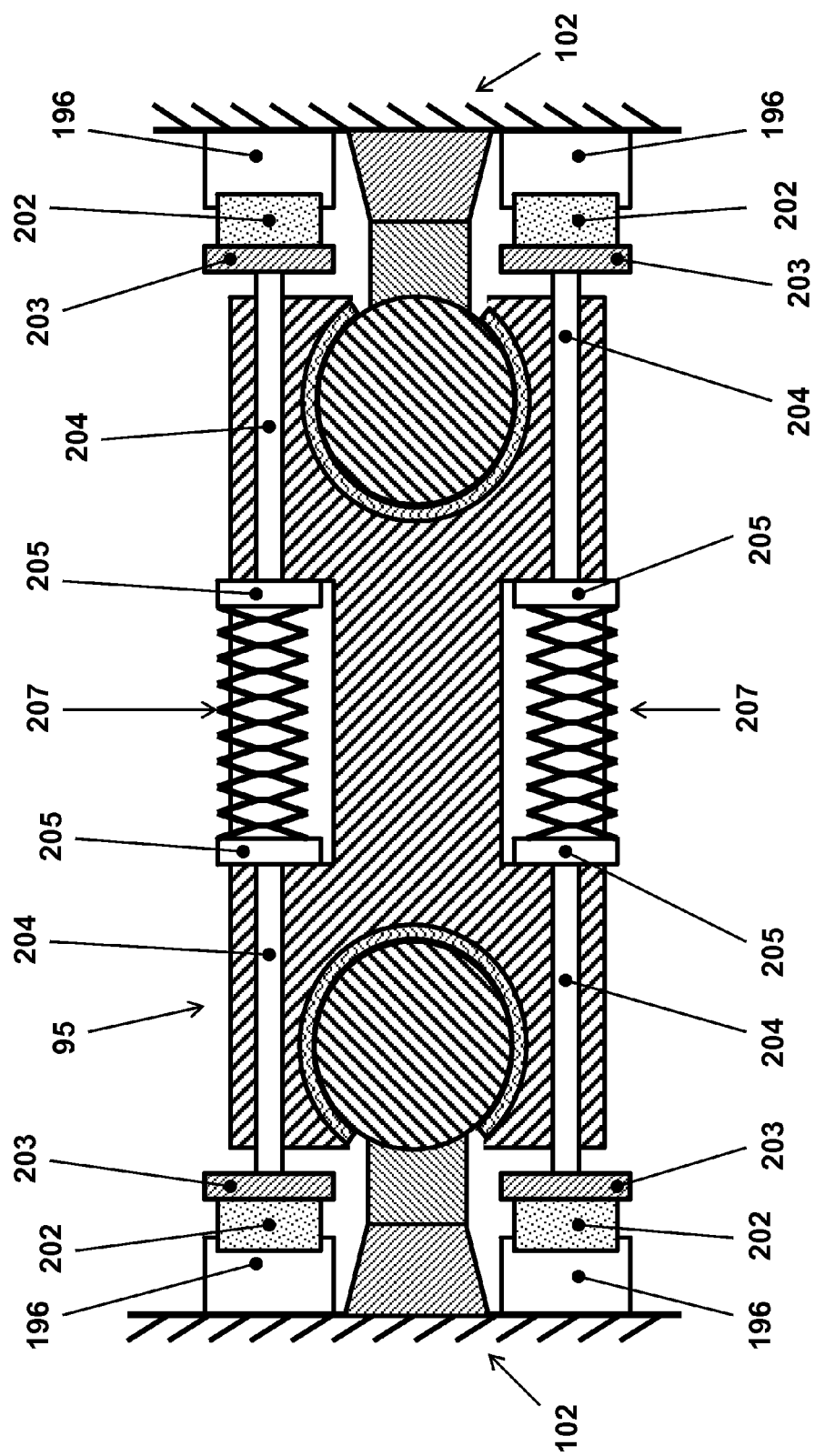
FIG. 30 illustrates a cross-sectional view of the mass element of the third embodiment 100 of FIG. 21 with braking mechanism of FIG. 22 with brake pad pressure equalizing mechanism.

The above brake pad pressure equalizing mechanism for the brake engagement mechanism of the mechanical shock testing machine embodiment 200 FIGS. 28 and 29 is shown in the schematic of FIG. 30. In this embodiment, all components that are shown are the same as those shown in FIGS. 28 and 29 except for the braking mechanism herein being described. In this braking mechanism, the braking pads 202 are fixedly attached to the relatively rigid backing supports 203, which are in turn fixed to the pins 204, which are free to slide through the corresponding guide holes provided in the mass element 95. The pins 204 are provided with heads 205 which would limit outward motion of the braking pads 202 to position the surfaces 201 (FIG. 29) of the braking pads 202 at proper distance from the surfaces 206 (FIG. 29) of the brake engaging elements 196 for proper engagement and brake pressure generation. Compressive springs 207 are then provided between the heads 205 of the pins 204 and are preloaded to appropriate levels so that as the brake pads 202 engage the brake engaging elements 196 as was previously described for the embodiment 200 (FIG. 29), the desired level of brake pressure is generated.

It will be appreciated by those skilled in the art that as the brake pads 202 engage the brake engaging elements 196, FIG. 30, the heads 205 of the pins 204 are pushed inward, thereby separating them from the mass element 95 surfaces with which they were in contact. As a result, the springs 207 are enabled to apply equal pressure to the corresponding brake pads 202.

In the schematic of FIG. 30, the basic method of equalizing brake pad pressure on either side of the mass element of the mechanical shock testing machine embodiment 200 of FIG. 28 is illustrated. It will, however, be appreciated by those skilled in the art that the same method can be applied to other similar embodiments, such as those of FIG. 22, FIGS. 25 and 26, and FIGS. 25 and 27 to achieve the same goal of equalizing brake pad pressure on both sides of the corresponding mass elements of the indicated mechanical shock testing machines.

It will also be appreciated by those skilled in the art that many other linkage mechanisms or hydraulic or pneumatic means commonly used in the art may also be used in place of springs 207 to achieve similar braking pad pressure equalization of the mechanism of FIG. 30.

It will be appreciated by those skilled in the art that similar to the mechanical shock testing machine embodiments 30 and 50 of FIGS. 2 and 5, respectively, the horizontally installed mechanical shock testing machine embodiments such as embodiments 100, 180 and 200 of FIGS. 12, 25 and 28, respectively, also allow for similar rapid and accurate setting of the braking force that is provided by their braking elements. The method and means of rapidly and accurately performing the brake force setting is as is described with reference to the schematic of FIG. 4 for the mechanical shock testing machine embodiment 30 of FIG. 2. Similar set up with means of applying force such as the indicated commonly used mechanical or hydraulic jack 44 which is similarly positioned between the machine structure and the braking elements may be used together with an intermediate force gage as was described for schematic of FIG. 4.

In all the above disclosed mechanical shock testing machine embodiments, the machines are provided with two rails over which the mass elements (for example, elements 23, 52 and 95 in the embodiments 30, 50 and 100 of FIGS. 2, 5 and 12) travel. It will, however, be appreciated by those skilled in the art that one or more than two rails may also be similarly used.

Figure 18:
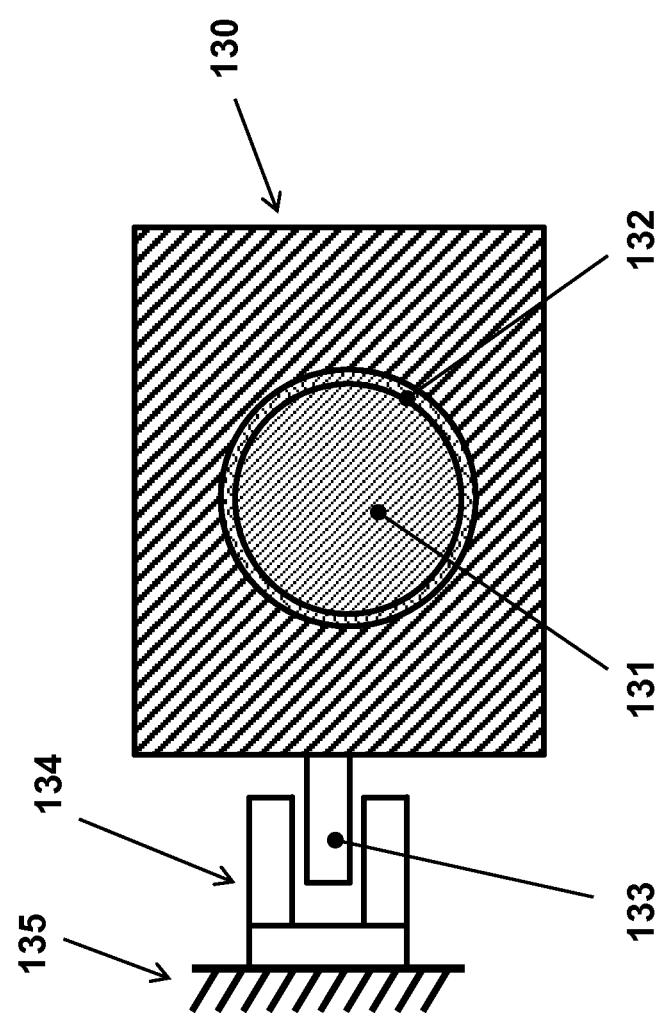
FIG. 18 illustrates a cross-sectional view of the rail, mass element and the anti-rotation guide for mechanical shock testing machines constructed with a single rail.

An advantage of using a single rail is that lighter mass elements may be used. The mass element however should be provided with a guide to prevent it from rotating about the rail when rails with circular cross-sections are used. This can, for example be accomplished as shown in the schematic of FIG. 18. In FIG. 18, the cross-sectional view of the mass element 130 is shown as assembled with a sleeve bearing 132 over the rail 131. The mass element 130 is also provided with an appendage 133 which rides inside the U-shaped guide 134, which is attached to the machine structure 135. As a result, as the mass element 130 travels along the length of the rail 131, the U-shaped guide 134 prevents the mass element 130 from rotating about the rail 131. A disadvantage of single rail mechanical shock testing machines is their limited surface for mounting components for shock testing. In particular, such machines cannot handle large and/or relatively heavy components since they have to be mounted on one side of the rail, subjecting the mass element and the test component to tipping accelerations and forces.

The use of more than two rails which are not co-planar to guide the mass element has several advantages. In general, all these advantages are achieved using three or at most four rails. The main advantage of using three or four rails that are not co-planar is that they would minimize the tendency for the mass element to tip over during the testing shock loading (deceleration pulse) due to usually unavoidable nonsymmetrical shock loading and/or mass distribution of the mass element and testing component assembly. The second advantage of using three or four rails that are not co-planar is that they could provide a significantly larger mass element surface area for testing component mounting, thereby can handle significantly larger components for shock testing.

Figure 19B:
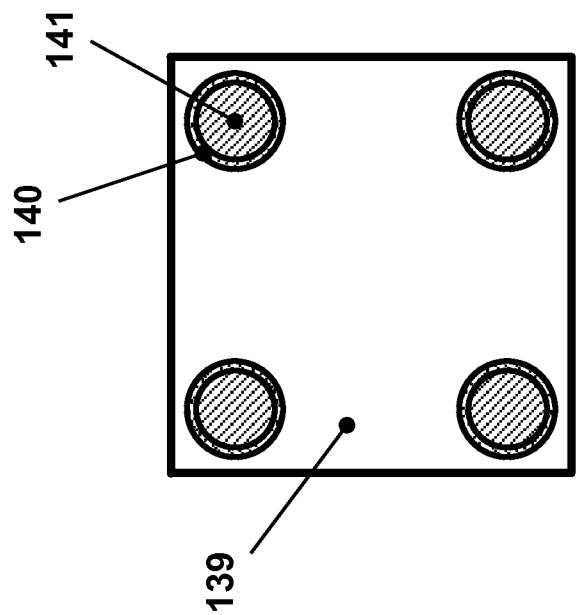
FIGS. 19A and 19B illustrate arrangements of the rails for mechanical shock testing machines constructed with three and four rails.
Figure 19A:
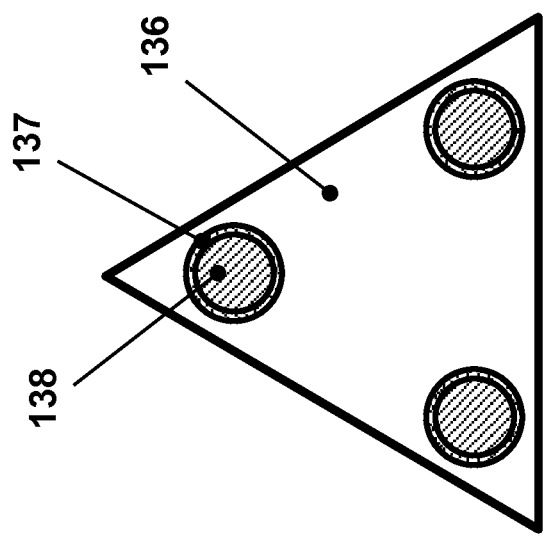

In general, since there is no advantage in using non-symmetrical positioning of the rails, the rails of a three-rail and four-rail mechanical shock testing machine can be positioned at equal distances, i.e., at the corners of an equilateral triangle and corners of a square, respectively, as shown in the schematics of FIGS. 19A and 19B, respectively. FIG. 19A shows an equilateral triangle arrangement of the rails 138 of a mechanical shock testing machine to accommodate a mass element 136 (which can be symmetrically shaped) with its sleeve bearing 137. FIG. 19B shows a rectangular arrangement of the rails 141 of a mechanical shock testing machine to accommodate a mass element 139 (which can be symmetrically shaped) with its sleeve bearing 140.

In the embodiments 50 and 100 of FIGS. 5 and 12, the braking elements 51 and 112, respectively, are shown to be separate units that are attached to the corresponding mass elements of the mechanical shock testing machines. It will be, however, appreciated by those skilled in the art that most of the disclosed braking element designs may be integrated into the mass elements of these machines. Such integrated mass element and braking element designs could significantly reduce the total decelerated mass (i.e., the total mass of the mass element and the braking elements). Such integrated mass element and braking element designs may be more cumbersome to assemble and maintain, particularly since the braking pads have to be regularly replaced in mechanical shock testing machines, particularly if they are used to perform relatively high G shock testing. As a result, the advantages and disadvantages of the integrated designs must be considered and matched against the frequency of use of the mechanical shock testing machine.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A shock testing machine comprising:
a movable impact mass upon which one or more components to test are mounted;
one or more rails upon which the impact mass is movable; and
a brake movably disposed on the one or more rails, the brake being movable independently relative to the movable impact mass, the brake being operatively engageable with the movable impact mass after the movable impact mass has moved a predetermined distance relative to the brake to retard the movement of the movable impact mass such that the components to be tested experience a deceleration profile.

2. The shock testing machine of claim 1, wherein the one or more rails comprises two or more rails.

3. The shock testing machine of claim 2, wherein the brake comprises a brake element corresponding to each of the two or more rails.

4. The shock testing machine of claim 1, wherein the brake is fixed to the movable impact mass.

5. The shock testing machine of claim 4, wherein the brake is movable on the one or more rails.

6. The shock testing machine of claim 1, wherein the one or more rails comprises two or more rails and the brake comprises a brake element corresponding to each of the two or more rails, the shock testing machine further comprising a rigid member connecting the brake elements such that the movable impact mass engages the brake elements at the same time after moving the predetermined distance.

7. The shock testing machine of claim 1, wherein the brake is disposed on the one or more rails at the predetermined distance from the movable impact mass and the brake is preset to be engaged with the one or more rails.

8. The shock testing machine of claim 1, wherein the brake is mounted on the movable impact mass and the brake is engaged with the one or more rails only after moving the predetermined distance.

9. The shock testing machine of claim 1, wherein the brake at least partially surrounds an outer periphery of the one or more rails.

10. The shock testing machine of claim 9, wherein the brake includes at least a circular portion for surrounding the outer periphery of the one or more rails.

11. The shock testing machine of claim 1, wherein the brake includes one or more first portions fixed to the movable impact mass that are engageable with one or more second portions fixed to a base structure.

12. The shock testing machine of claim 1, wherein the brake includes a cable having one end fixed to a base structure and another end removably connected to the brake, wherein the brake is engaged by movement of the movable impact mass through the predetermined distance tending to pull the another end from the brake.

13. The shock testing machine of claim 1, wherein the rails are positioned vertically such that gravity assists the movement of the movable impact mass.

14. The shock testing machine of claim 1, wherein the rails are positioned horizontally such that gravity does not assist the movement of the movable impact mass.

15. The shock testing machine of claim 1, wherein the movable impact mass includes a pocket for housing the one or more components to be tested.

16. The shock testing machine of claim 1, wherein the one or more rails comprises two or more rails and the brake comprises a brake element corresponding to each of the two or more rails, the shock testing machine further comprising a mechanism for applying equal pressure to each of the brake elements.

17. A method for shock testing one or more components, the method comprising:
mounting the one or more components to a movable impact mass;
movably disposing the movable impact mass on one or more rails;
movably disposing a brake on the one or more rails so as to be movable independently of the movable impact mass;
moving the movable impact mass a predetermined distance; and
engaging the brake after the movable impact mass has moved a predetermined distance relative to the brake to retard the movement of the movable impact mass such that the components to be tested experience a deceleration profile.

18. The method of claim 17, wherein the brake is disposed on the one or more rails at the predetermined distance from the movable impact mass and the brake is preset to be engaged with the one or more rails.

19. The method of claim 17, wherein the brake is mounted on the movable impact mass and the brake is engaged with the one or more rails only after moving the predetermined distance.

* * * * *